US008580537B2

(12) United States Patent
Suzuki et al.

(10) Patent No.: US 8,580,537 B2
(45) Date of Patent: Nov. 12, 2013

(54) THERMOTOLERANT TRANSGLUTAMINASE ORIGINATING IN ACTINOMYCES

(75) Inventors: Mototaka Suzuki, Kawasaki (JP); Masayo Date, Kawasaki (JP); Keiichi Yokoyama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 84 days.

(21) Appl. No.: 13/225,698

(22) Filed: Sep. 6, 2011

(65) Prior Publication Data

US 2012/0021458 A1 Jan. 26, 2012

Related U.S. Application Data

(63) Continuation of application No. PCT/JP2010/053683, filed on Mar. 5, 2010.

(30) Foreign Application Priority Data

Mar. 6, 2009 (JP) .................................. 2009-053537

(51) Int. Cl.
   *C12N 9/10* (2006.01)
(52) U.S. Cl.
   USPC ........................ 435/68.1; 435/193; 435/252.3
(58) Field of Classification Search
   USPC .................................... 435/68.1, 193, 252.32
   See application file for complete search history.

(56) References Cited

U.S. PATENT DOCUMENTS

| 7,704,707 B2 | 4/2010 | Umezawa et al. |
| 2004/0002144 A1 | 1/2004 | Kashiwagi et al. |
| 2005/0064571 A1 | 3/2005 | Lin et al. |
| 2007/0184525 A1 | 8/2007 | Date et al. |
| 2009/0117640 A1 | 5/2009 | Norskov-Lauritsen et al. |
| 2009/0318349 A1 | 12/2009 | Hu et al. |
| 2010/0143970 A1 | 6/2010 | Yokoyama et al. |
| 2010/0159560 A1 | 6/2010 | Umezawa et al. |
| 2011/0137007 A1 | 6/2011 | Suzuki et al. |

FOREIGN PATENT DOCUMENTS

| EP | 1219713 | 7/2002 |
| JP | 2008-194004 | 8/2008 |
| WO | WO96/06931 | 3/1996 |
| WO | WO02/14518 | 2/2002 |
| WO | WO2008/020074 | 2/2008 |
| WO | WO2008/099898 | 8/2008 |
| WO | WO2009/016257 | 2/2009 |

OTHER PUBLICATIONS

Burgess et al., Journal of Cell Biology, Nov. 1990, vol. 111, pp. 2129-2138.*
Lazar et al., Molecular and Cellular Biology, Mar. 1988, vol. 8, No. 3, pp. 1247-1252.*
Schwartz et al., Proc. Natl. Acad. Sci. USA, vol. 1987; 84:6408-6411.*
Lin et al., Biochemistry, 1975, vol. 14, pp. 1559-1563.*
Acland et al., Nature, 1990, vol. 343, pp. 662-665.*
Lorand et al., Transglutaninases: Crosslinking enzymes with pleiotropic functions. Nature Reviews. 4: 140-156, 2003.*
Lin, Y.-S., et al., "Cloning of the gene coding for transglutaminase from *Streptomyces platensis* and its expression in *Streptomyces lividans*," Process Biochem. 2006;41:519-524.
Supplementary European Search Report for EP Patent App. No. 10748849.6 (Dec. 14, 2011).
Marx, C. K., et al., "Random mutagenesis of a recombinant microbial transglutaminase for the generation of thermostable and heat-sensitive variants," J. Biotechnol. 2008;136:156-162.
Yokoyama, K., et al., "Screening for improved activity of a transglutaminase from *Streptomyces mobaraensis* created by a novel rational mutagenesis and random mutagenesis," Appl. Microbiol. Biotechnol. 2010;87:2087-2096.
International Search Report for PCT Patent App. No. PCT/JP2010/053683 (Jun. 8, 2010).
Tagami, U., et al., "Substrate specificity of microbial transglutaminase as revealed by three-dimensional docking simulation and mutagenesis," Protein Eng. Des. Sel. 2009;22(12):747-752.

* cited by examiner

*Primary Examiner* — Tekchand Saidha
*Assistant Examiner* — Rama P Ramanujam
(74) *Attorney, Agent, or Firm* — Shelly Guest Cermak Cermak Nakajima LLP

(57) ABSTRACT

The present invention provides transglutaminases with improved heat resistance. Specifically, the present invention provides mutant transglutaminase proteins with improved heat resistance as obtained by introducing appropriate mutations into transglutaminases, which results in the incorporation of a disulfide bond.

18 Claims, 8 Drawing Sheets

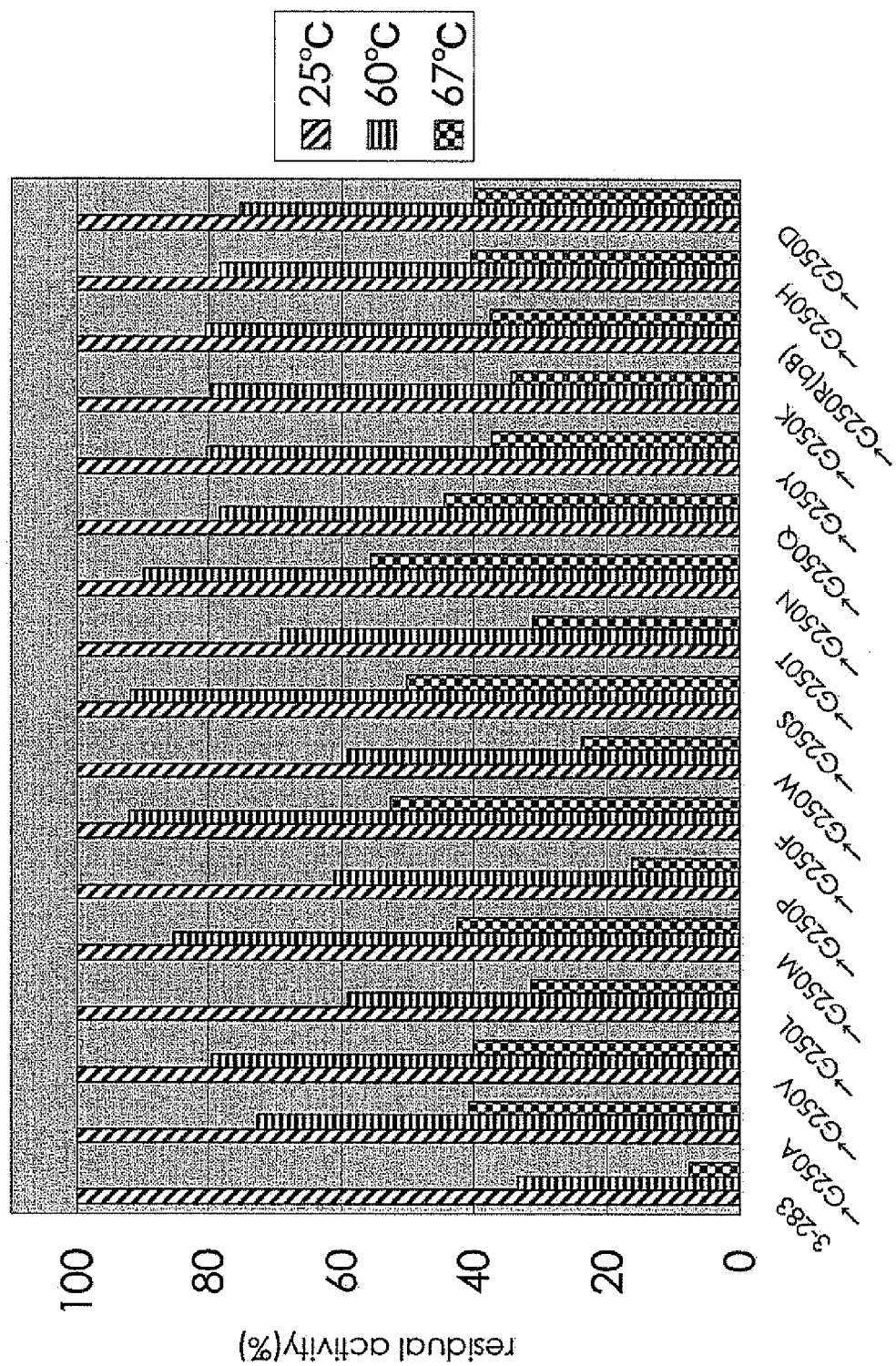

THERMOTOLERANT TRANSGLUTAMINASE ORIGINATING IN ACTINOMYCES

This application is a Continuation of, and claims priority under 35 U.S.C. §120 to PCT/JP2010/053683, filed Mar. 5, 2010, and claims priority therethrough under 35 U.S.C. §119 to Japanese Application No. 2009-053537, filed Mar. 6, 2009, the entireties of which are incorporated by reference herein. Also, the entirety of the Sequence Listing filed electronically herewith is hereby incorporated by reference herein (File name: 2011-09-06T_US-467_Seq_List; File size: 46 KB; Date recorded: Sep. 6, 2011).

BACKGROUND OF THE INVENTION

1. Field of the Invention

The present invention relates to mutant transglutaminase (TG) proteins of actinomycetous origin. Transglutaminase (also simply referred to as "TG") is widely utilized for food processing and the like since it catalyzes the formation of a cross-linking bond between proteins, resulting in a gel-like substance. TGs which are mutated to improve transglutaminase activity or thermal stability can help to reduce the amount of TG required and can be used at high temperatures, thus making it possible to apply this enzyme to new fields.

2. Brief Description of the Related Art

Transglutaminase is an enzyme that catalyzes the acyl transfer reaction of the γ-carboxamide group in a peptide chain of a protein. When this enzyme is allowed to act on a protein, a reaction to form the ε-(γ-Glu)-Lys cross-linking and a reaction to replace Gln with Glu by deamidation can occur. Transglutaminases of animal origin and those of microbial origin have been reported to date. Those of animal origin are $Ca^{2+}$-dependent, and distributed in animal organs, skin, blood, and the like. For example, guinea pig liver transglutaminase (K. Ikura et al. Biochemistry, 27, 2898, 1988), human epidermal keratinocyte transglutaminase (M. A. Phillips et al. Proc. Natl. Acad. Sci. U.S.A., 87, 9333, 1990), human blood coagulation factor XIII (A. Ichinose et al, Biochemistry, 25, 6900, 1986), and the like have been reported. TGs of microbial origin that are non-$Ca^{2+}$-dependent have been reported in bacteria of the genus *Streptoverticillium*. Examples include *Streptoverticillium griseocameum* IFO 12776, *Streptoverticillium cinnamoneum* sub sp. *cinnamoneum* IFO 12852, *Streptoverticillium mobaraense* IFO 13819, and the like. The transglutaminase found in a culture supernatant of a variant of *Streptoverticillium mobaraense*, in particular, is referred to as MTG (Microbial Transglutaminase). Furthermore, a $Ca^{2+}$-independent transglutaminase has also been discovered in *Streptomyces lydicus* NRRL B-3446 (JP-A-H10-504721). It has been found, as a result of peptide mapping and gene structural analysis, that the primary structures of the transglutaminases produced by these microorganisms are not homologous at all with those of animal origin (EP-A-0481504 A1).

MTG is a monomeric protein consisting of 331 amino acids, and having a molecular weight of about 38,000 (T Kanaji et al, Journal of Biological Chemistry. 268, 11565, 1993). Because MTG is often purified from a culture of one of the aforementioned microorganisms and the like, there have been problems with respect to the amount supplied, efficiency, and the like. Attempts have also been made to produce transglutaminase by genetic engineering techniques. A method based on secretory expression by *Escherichia coli* (*E. coli*), yeast and the like (JP-A-H5-199883), a method wherein *Escherichia coli* is allowed to express MTG as a protein inclusion body after which this inclusion body is solubilized with a protein denaturant, treated to remove the denaturant, and then reconstituted to produce active MTG (JP-A-H6-30771), and a method for secretory expression of MTG using *Corynebacterium glutamicum* (WO2002/081694) have been reported. Unlike transglutaminases of animal origin, MTG and other transglutaminases of microbial origin are $Ca^{2+}$-independent, and are hence utilized for production of gelled foods such as jellies, yogurt, cheese, or gel-based cosmetics and the like, as well as for improving the quality of meat and the like (JP-A-64-27471). MTG is also utilized for production of raw materials for heat-stable microcapsules, carriers for immobilized enzymes and the like, and so is industrially highly useful. Regarding enzymatic reaction conditions, a gelled food, for example, does not set if the enzymatic reaction time is short, and conversely, if the reaction time is too long, the gelled food becomes too hard to be a commercial product. Hence, when MTG is utilised for production of gelled foods such as jellies, yogurt, cheese, or gel-based cosmetics and the like, or to improve the quality of meat and the like, the desired product is prepared by adjusting substrate and enzyme concentrations, reaction temperature, and reaction time. However, as foods, reagents and the like, which can be produced by utilizing MTG, have become increasingly diverse, in some instances the desired product cannot be prepared solely by adjusting concentrations, temperature, time and the like; therefore, there is a need to modify the enzymatic activity of MTG.

Wild-type MTG (wild-type MTG means an MTG that occurs naturally and has not undergone a modification in its amino acid sequence) is known to be stable at pH between about 4 and 10, and can be stable over a relatively broad range of pH, but under extremely acidic or alkaline conditions, wild-type MTG loses its activity. The optimum temperature for wild-type MTG is about 50° C., and it also loses activity if the temperature is too high. Even at temperatures lower than the optimum temperature, incubation for a long time can result in reduced enzymatic activity. Therefore, a transglutaminase which has been mutated to improve pH stability, thermal stability, and the like will be expected to allow for the use of transglutaminase for new purposes.

MTG has been utilised mainly in the food area so far. Feasibility of application in a wide variety of uses, including textiles, chemical products (photographic films, tanning), feeds, cosmetics, and pharmaceuticals, has been suggested.

In the textile area, wool modification with transglutaminase has been reported. Specifically, it is known that by treating wool with transglutaminase, anti-shrinkage quality, anti-pilling quality, and hydrophobicity can be conferred while maintaining the original texture (JP-A-H3-213574). When transglutaminase is used in wool manufacture and processing, a reaction to keratin at a high temperature in a short time would increase throughput per unit time and improve production efficiency, and therefore, is thought to be industrially useful.

Tanning refers to a processing wherein an animal hide/skin is subjected to a series of treatments and processing consisting of a plurality of steps to render the hide/skin a durable, flexible leather; this processing is achieved by cross-linking the collagen of the hide/skin with hexavalent chromium. Because hexavalent chromium is harmful and the release thereof into the environment is unwanted, there is strong demand for the development of an alternative method. Regarding the utilisation of transglutaminase for tanning, U.S. Pat. No. 6,849,095 discloses that a transglutaminase of microbial origin can be used for tanning, but discloses no examples of actually allowing the transglutaminase to act on a hide/skin; a transglutaminase has not yet been in practical application for this purpose. Because cross-linking with hexavalent chromium takes place at pH 3 to 4, transglutaminase is also likely able to react at this pH, but because MTG is labile to acidity, actual application is difficult.

Hence, in the case of applications such as textile processing and tanning, it is desirable that the thermal stability (i.e., heat resistance) of transglutaminase be improved to complete the reaction at high temperature in a short time, and that the pH stability be improved to allow the reaction in to proceed under acidic conditions.

As stated above, improving the thermal and pH stability of transglutaminase is possible by modification, and thereby improving the enzymatic activity of the transglutaminase. For example, improving the thermal stability may allow for a possible increase in reaction rates and the like. Also, improving the pH stability will allow the enzymatic reaction to proceed over a broader range of pH values, and the product can be stored also over a broader range of pH values. This will also be advantageous in industrialization.

To modify the heat resistance and/or pH stability of transglutaminase, it is necessary to prepare a mutant of the transglutaminase and evaluate the activity and the like thereof. To prepare a mutant, it is necessary to manipulate the wild-type gene; therefore, a recombinant protein must be prepared. In the case of MTG, a secretory expression system using *Corynebacterium glutamicum* has been established (WO2002/081694).

To increase the stability of a protein, it is generally possible to introduce a non-covalent bond such as a hydrogen bond, a covalent bond such as a disulfide bond, or an electrostatic or hydrophobic interaction to enhance the packing of the hydrophobic core within the molecule. Other methods include stabilizing the a helix in the secondary structure, or removing factors that make the structure of the protein unstable. To increase the stability of a protein by introducing a disulfide bond, it is necessary to determine positions suitable for introducing cysteine. In the case of MTG, mutated transglutaminases whose heat resistance and/or pH stability is improved by introducing a disulfide bond have been created (WO2008/099898).

WO2008/099898 discloses mutated transglutaminases prepared by introducing a disulfide bond into the wild-type transglutaminase, and the like. For example, WO2008/099898 discloses proteins possessing transglutaminase activity which have at least a set of mutations selected from among:
  a) substitution of 7-position and 58-position to cysteine,
  b) substitution of 46-position and 318-position to cysteine,
  c) substitution of 93-position and 112-position to cysteine,
  d) substitution of 106-position and 213-position to cysteine,
  e) substitution of 160-position and 228-position to cysteine,
  f) substitution of 2-position and 282-position to cysteine,
  g) substitution of 2-position and 283-position to cysteine,
  h) substitution of 3-position and 283-position to cysteine, and
  i) substitution of 17-position and 330-position to cysteine,
in the sequence of MTG, polynucleotides that encode the proteins, recombination vectors including one of the polynucleotides, host cells transformed with one of the vectors, a method of producing a transglutaminase by culturing the host cells, and the like. This reference also discloses a method for processing a substrate protein using the described mutated transglutaminase.

However, although some improvements in the heat resistance and/or pH stability were observed in mutated transglutaminases containing disulfide bonds, further improvement of the heat resistance is desired so that the proteins can endure high temperatures used for textile processing and the like.

To modify the enzyme activity of a mutated transglutaminase containing one or more disulfide bonds, it is necessary to prepare a mutant thereof and evaluate the activity and the like thereof. To prepare a mutant, it is necessary to manipulate the wild-type gene; therefore, a recombinant protein must be prepared. In the case of MTG, a secretory expression system using *Corynebacterium glutamicum* has been established (WO2002/081694).

Although C. K. Marx et al, Journal of Biotechnology, 136 (3), p. 156-162, September 2008 describes some MTG mutants, the heat resistances of these mutants are inadequate for use at high temperatures like those used for textile processing and the like.

SUMMARY OF THE INVENTION

Problems to be Solved by the Invention

It is an aspect of the present invention to provide transglutaminase mutant proteins with improved heat resistance as compared with wild-type (hereinafter, also simply abbreviated as WT) transglutaminase and the mutated transglutaminases prepared by introducing a disulfide bond into WT transglutaminase, or those described in WO2008/099898 (hereinafter, also simply referred to as "disulfide bond-introduced transglutaminases"), and thereby enable an enzyme reaction at high temperatures in a short time.

Means of Solving the Problems

The present inventors extensively investigated to solve the above-described problems, and as a result, provide transglutaminase mutant proteins with improved heat resistance compared with the original disulfide bond-introduced transglutaminase by further introducing mutations into the disulfide bond-introduced transglutaminase genes described in WO2008/099898. Mutant proteins of the present invention enable an enzyme reaction at high temperatures in a short time, and are suitable for textile processing, tanning and the like.

The present invention can be outlined as described below.

It is an aspect of the present invention to provide a protein having transglutaminase activity, and comprising an amino acid sequence selected from the group consisting of:
  (A) the amino acid sequence of SEQ ID NO: 2, but comprising a mutation at a position selected from the group consisting of the 101-position, 157-position, 250-position, and combinations thereof;
  (B) the amino acid sequence recited in (A), but comprising a substitution, deletion, addition and/or insertion of one or several residues at a position other than the 101-position, 157-position, and 250-position;
  (C) the amino acid sequence selected from the group consisting of SEQ ID NO: 4, 6, 8, 10, and 12, but comprising a mutation at a position corresponding to a position in SEQ ID NO: 2 selected from the group consisting of the 101-position, 157-position, 250-position, and combinations thereof;
  (D) an amino acid sequence which is at least 70% homologous to the amino acid sequence selected from the group consisting of SEQ ID NO: 2, 4, 6, 8, 10, and 12, but comprising a mutation at a position corresponding to a position in SEQ ID NO: 2 selected from the group consisting of the 101-position, 157-position 250-position, and combinations thereof;
(E) the amino acid sequence of (C), but comprising a substitution, deletion, addition and/or insertion of one or several residues at a position corresponding to a position in SEQ ID NO: 2 other than the 101-position, 157-position, and 250-position; and
(F) the amino acid sequence of (D), but comprising a substitution, deletion, addition, and/or insertion of one or several residues at a position corresponding to a position in SEQ ID NO: 2 other than the 101-position, 157-position, and 250-position.

It is a further aspect of the present invention to provide the protein as described above, further comprising a mutation to cysteine at a set of positions selected from the group consisting of:
a) the 3-position and 283-position,
b) the 2-position and 282-position,
c) the 2-position and 283-position,
d) the 7-position and 58-position, and
e) combinations thereof.

It is a further aspect of the present invention to provide a protein having transglutaminase activity, and comprising an amino acid sequence selected from the group consisting of:
(A) the amino acid sequence of SEQ ID NO: 2, but having a mutation to cysteine at the 3-position and 283-position, and also having a mutation at a position selected from the group consisting of the 101-position, 157-position, 250-position, and combinations thereof;
(B) the amino acid sequence recited in (A), but comprising a substitution, deletion, addition and/or insertion of one or several residues at a position other than the 3-position, 101-position, 157-position, 250-position and 283-position;
(C) the amino acid sequence selected from the group consisting of SEQ ID NO: 4, 6, 8, 10 and 12, but having a mutation to cysteine at positions corresponding to positions in SEQ ID NO: 2 of the 3-position and 283-position, and also having a mutation at a position corresponding to a position in SEQ ID NO:2 selected from the group consisting of the 101-position, 157-position, 250-position, and combinations thereof;
(D) an amino acid sequence which is at least 70% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof;
(E) the amino acid sequence of (C), but comprising a substitution, deletion, addition and/or insertion of one or several residues at a position corresponding to a position in SEQ ID NO: 2 other than the 3-position, 101-position, 157-position, 250-position and 283-position; and
(F) the amino acid sequence of (D), but comprising a substitution, deletion, addition, and/or insertion of one or several residues at a position corresponding to a position in SEQ ID NO: 2 other than the 3-position, 101-position, 157-position, 250-position and 283-position.

It is a further aspect of the present invention to provide a protein having transglutaminase activity, and comprising the amino acid sequence selected from the group consisting of:
(A) the amino acid sequence of SEQ ID NO: 2, but having a mutation to cysteine at the 2-position and 282-position, and also having a mutation at a position selected from the group consisting of the 101-position, 157-position, 250-position, and combinations thereof;
(B) the amino acid sequence recited in (A), but comprising a substitution, deletion, addition and/or insertion of one or several residues at a position other than the 2-position, 101-position, 157-position, 250-position, and 282-position;
(C) the amino acid sequence selected from the group consisting of SEQ ID NO: 4, 6, 8, 10 and 12, but having a mutation to cysteine at positions corresponding to positions in SEQ ID NO: 2 of the 2-position and 282-position, and also having a mutation of a position corresponding to a position in SEQ ID NO: 2 selected from the group consisting of the 101-position, 157-position, 250-position, and combinations thereof;
(D) an amino acid sequence which is at least 70% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof;
(E) the amino acid sequence of (C), but comprising a substitution, deletion, addition and/or insertion of one to several residues at a position corresponding to a position in SEQ ID NO: 2 other than the 2-position, 101-position, 157-position, 250-position and 282-position; and
(F) the amino acid sequence of (D), but comprising a substitution, deletion, addition, and/or insertion of one or several residues at a position corresponding to a position in SEQ ID NO: 2 other than the 2-position, 101-position, 157-position, 250-position and 282-position.

It is a further aspect of the present invention to provide a protein having transglutaminase activity, and comprising the amino acid sequence selected from the group consisting of:
(A) the amino acid sequence of SEQ ID NO: 2, but having a mutation to cysteine at the 2-position and 283-position, and also having a mutation at a position selected from the group consisting of the 101-position, 157-position, 250-position, and combinations thereof; ¥
(B) the amino acid sequence recited in (A), but comprising a substitution, deletion, addition and/or insertion of one or several residues at a position other than the 2-position, 101-position, 157-position, 250-position, and 283-position;
(C) the amino acid sequence selected from the group consisting of SEQ ID NO: 4, 6, 8, 10, and 12, but having a mutation to cysteine at positions corresponding to positions in SEQ ID NO: 2 of the 2-position and 283-position, and also having a mutation at a position corresponding to a position in SEQ ID NO: 2 selected from the group consisting of the 101-position, 157-position, 250-position, and combinations thereof;
(D) an amino acid sequence which is at least 70% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof;
(E) the amino acid sequence as recited in (C), but comprising a substitution, deletion, addition and/or insertion of one or several residues at a position corresponding to a position in SEQ ID NO: 2 other than the 2-position, 101-position, 157-position, 250-position and 283-position; and (F) the amino acid sequence of (D), but comprising a substitution, deletion, addition, and/or insertion of one or several residues at a position corresponding to a position in SEQ ID NO: 2 other than the 2-position, 101-position, 157-position, 250-position and 283-position.

It is a further aspect of the present invention to provide a protein having transglutaminase activity, and comprising an amino acid sequence selected from the group consisting of:
(A) the amino acid sequence of SEQ ID NO: 2, but having a mutation to cysteine at the 7-position and 58-position, and also having a mutation at a position selected from the group consisting of the 101-position, 157-position, 250-position, and combinations thereof;
(B) the amino acid sequence recited in (A), but comprising a substitution, deletion, addition and/or insertion of one or several residues at a position other than the 7-position, 58-position, 101-position, 157-position, and 250-position;
(C) the amino acid sequence selected from the group consisting of SEQ ID NO: 4, 6, 8, 10, and 12, but having a mutation to cysteine at positions corresponding to positions in SEQ ID NO: 2 of the 7-position and 58-position, and also having a mutation at a position corresponding to a position in SEQ ID NO: 2 selected from the group consisting of the 101-position, 157-position, 250-position, and combinations thereof;
(D) an amino acid sequence which is at least 70% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof;
(E) the amino acid sequence of (C), but comprising a substitution, deletion, addition and/or insertion of one or several residues at a position corresponding to a position in SEQ ID NO: 2 other than the 7-position, 58-position, 101-position, 157-position, and 250-position; and
(F) the amino acid sequence of (D), but comprising a substitution, deletion, addition, and/or insertion of one or several residues at a position corresponding to a position in SEQ ID NO: 2 other than the 7-position, 58-position, 101-position, 157-position, and 250-position.

It is a further aspect of the present invention to provide the protein as described above, wherein the mutation at the 101-position is a mutation to proline, the mutation at the 157-position is a mutation to alanine or serine, the mutation at the 250-position is a mutation to alanine or arginine.

It is a further aspect of the present invention to provide the protein as described above, wherein the protein has a mutation of the aspartic acid at the 3-position to cysteine, a mutation of the serine at the 101-position to proline, a mutation of the glycine at the 157-position to serine, a mutation of glycine at the 250-position to arginine, and a mutation of the glycine at the 283-position to cysteine.

It is a further aspect of the present invention to provide the protein as described above, wherein the protein further has a set of mutations selected from the group consisting of:
(1) mutation of 101-position from serine to proline, mutation of 157-position from glycine to serine, and mutation of 250-position from glycine to an amino acid selected from the group consisting of alanine, valine, leucine, methionine, proline, phenylalanine, tryptophan, serine, threonine, asparagine, glutamine, tyrosine, lysine, arginine, histidine, and aspartic acid;
(2) mutation of 157-position from glycine to serine, mutation of 250-position from glycine to arginine, and mutation of 101-position from serine to an amino acid selected from the group consisting of glycine, alanine, valine, isoleucine, proline, phenylalanine, asparagine, glutamine, tyrosine, lysine, arginine, and glutamic acid; and
(3) mutation of 101-position from serine to proline, mutation of 250-position from glycine to arginine, and mutation of 157-position from glycine to an amino acid selected from the group consisting of alanine, valine, isoleucine, serine, asparagine, lysine, arginine, histidine, aspartic acid and glutamic acid.

It is a further aspect of the present invention to provide the protein as described above, wherein the protein further has mutation of 101-position from serine to proline; mutation of 157-position from glycine to alanine, serine or arginine; and mutation of 250-position from glycine to alanine, phenylalanine, serine, asparagine or arginine.

It is a further aspect of the present invention to provide the protein as described above, wherein the protein further has a set of mutations selected from the group consisting of:
(1) mutation of 101-position from serine to proline, mutation of 157-position from glycine to serine, and mutation of 250-position from glycine to alanine, phenylalanine, serine, asparagine or arginine;
(2) mutation of 157-position from glycine to serine, mutation of 250-position from glycine to arginine, and mutation of 101-position from serine to proline; and
(3) mutation of 101-position from serine to proline, mutation of 250-position from glycine to arginine, and mutation of 157-position from glycine to alanine, serine or arginine.

It is a further aspect of the present invention to provide the protein as described above, wherein the protein further comprises mutation of the 208-position from arginine to leucine, alanine, or glutamic acid.

It is a further aspect of the present invention to provide the protein as described above, wherein the protein further comprises:
(1) mutation of 208-position from arginine to tryptophan,
(2) mutation of 268-position from aspartic acid to asparagine,
(3) mutation of 132-position from valine to leucine,
(4) mutation of 238-position from arginine to methionine, or
(5) mutation of 249-position from glutamic acid to lysine.

It is a further aspect of the present invention to provide a polynucleotide that encodes the protein as described above.

It is a further aspect of the present invention to provide a recombinant vector comprising the polynucleotide as described above.

It is a further aspect of the present invention to provide a host cell transformed with the recombinant vector as described above.

It is a further aspect of the present invention to provide a method of producing a protein comprising culturing the host cell as described above, and collecting a protein possessing transglutaminase activity.

It is a further aspect of the present invention to provide a method of processing a substrate protein, comprising the step of allowing a protein produced by the method as described above to act on a substrate protein.

It is a further aspect of the present invention to provide a method of processing a substrate protein, comprising the step of allowing the host cell as described above to act on a substrate protein.

It is a further aspect of the present invention to provide the method as described above, wherein the processing of a substrate protein is performed at 40° C. to 100° C.

Effect of the Invention

According to the present invention, it is possible to provide transglutaminases with further improved heat resistance by modifying conventional disulfide bond-introduced transglutaminases (particularly disulfide bond-introduced MTGs). Furthermore, novel products and novel technologies can be provided by using a transglutaminase with improved heat resistance.

BRIEF DESCRIPTION OF THE DRAWINGS

FIG. 4C is a graphic representation showing the results of an evaluation of the heat resistances in mutants listed in Table 6.

Figure 1:
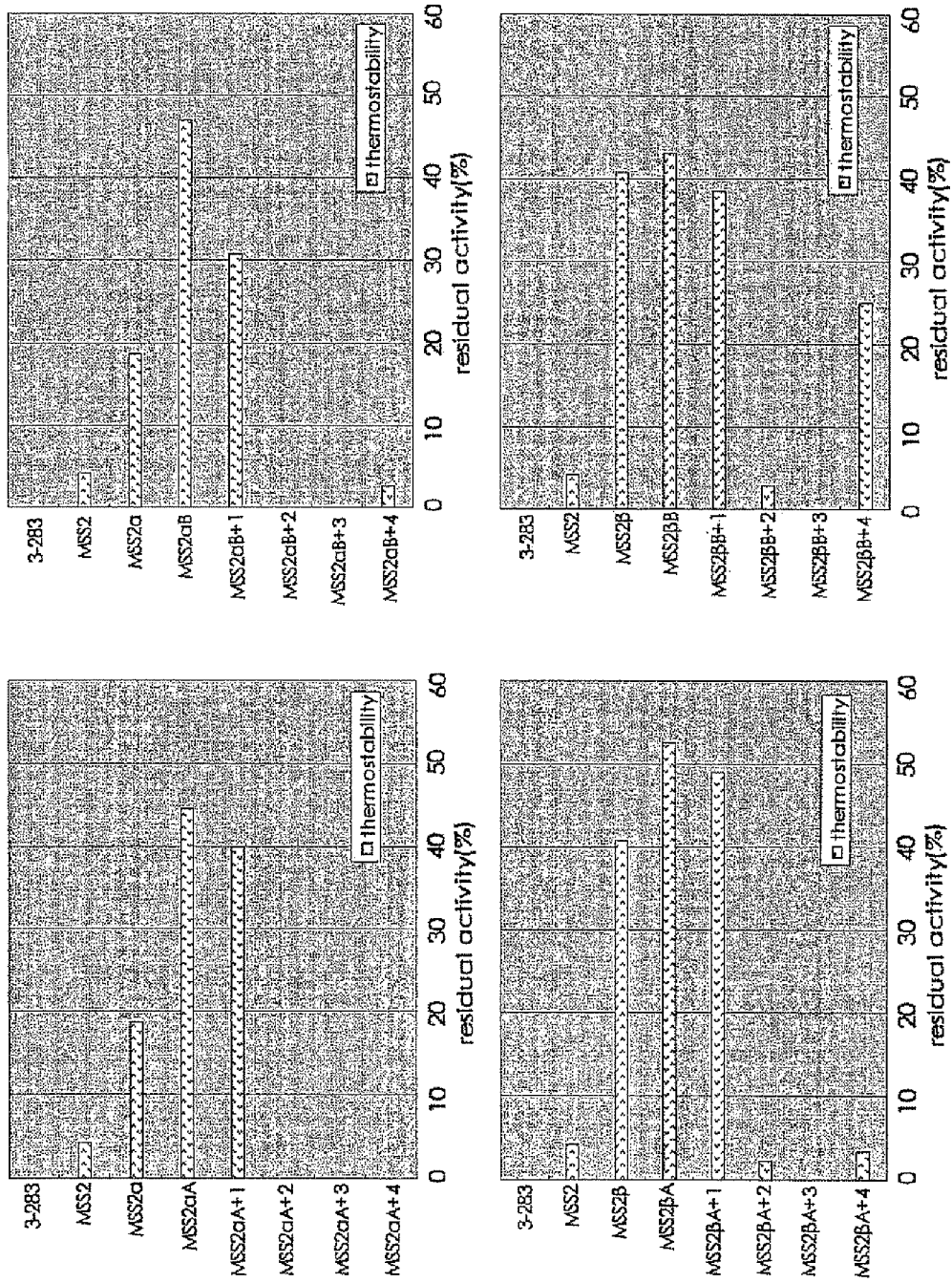
FIG. 1 is a graphic representation showing the heat resistances (residual activities) of multiple mutants derived from disulfide bond-introduced transglutaminase.

DESCRIPTION OF THE PREFERRED
EMBODIMENTS

Transglutaminase is widely utilized for the production of foods such as gelatin, cheese, yogurt, tofu, kamaboko, hams, sausages, and noodles, as well as for improving the quality of meat and the like (JP-A-SHO-64-27471). Transglutaminase is an enzyme often used in industry, and it has been utilized for the production of raw materials for heat-stable microcapsules, carriers for immobilized enzymes and the like. Transglutaminase catalyzes the acyl transfer reaction of the γ-carboxamide group on a glutamine residue in the peptide chain of a protein molecule. When the ε-amino group of a lysine residue in a protein molecule acts as an acyl receptor, an ε-(γ-Glu)-Lys bond is formed in the protein molecule and between the molecules.

Transglutaminases are roughly divided into $Ca^{2+}$-dependent ones, which are of animal origin, and $Ca^{2+}$-independent ones, which are of microbial origin. TGs of microbial origin which have been reported include those derived from actinomycetes. Examples of nucleotide sequences and amino acid sequences of actinomycete-derived TGs are shown in the table below.

TABLE 1

Names, nucleotide sequences and amino acid sequences of actinomycetes

| Actinomycete | Nucleotide sequence | Amino acid sequence |
|---|---|---|
| Streptomyces mobaraensis | SEQ ID NO: 1 | SEQ ID NO: 2 |
| Streptomyces cinnamoneus | SEQ ID NO: 3 | SEQ ID NO: 4 |
| Streptomyces fradiae | SEQ ID NO: 5 | SEQ ID NO: 6 |
| Streptomyces ladakanum | SEQ ID NO: 7 | SEQ ID NO: 8 |
| Streptomyces lydicus | SEQ ID NO: 9 | SEQ ID NO: 10 |
| Streptomyces platensis | SEQ ID NO: 11 | SEQ ID NO: 12 |

Even when using a transglutaminase homologue from a microorganism other than these, a mutant protein with improved heat resistance can be obtained according to the method described herein. Specifically, because transglutaminases can have slightly different sequences depending on the microbial species and strains from which they are derived, the amino acid sequences of transglutaminases that can be modified to obtain mutant proteins are not limited to the amino acid sequences shown in SEQ ID Nos. 2, 4, 6, 8, 10 and 12; but can include any protein possessing transglutaminase activity which is 70%, 80%, 90%, 95%, or even 98% or more homologous, to SEQ ID NOs: 2, 4, 6, 8, 10 or 12. The mutant proteins as described herein can be obtained by performing an alignment in the same manner as the method described below, and identifying a corresponding amino acid residue, and finally introducing a mutation of the amino acid residue. As used herein, "homology" refers to identity.

For homology analysis, calculations can be made using, for example, the default parameters of "Genetyx ver. 7 (Genetyx Corporation)".

Furthermore, a polynucleotide that hybridizes with a sequence complementary to the nucleotide sequence shown by the aforementioned SEQ ID NOs: 1, 3, 5, 7, 9 or 11, or a probe that can be prepared from these sequences, under stringent conditions, and that encodes a protein possessing transglutaminase activity, can also be used to prepare a mutant protein.

Herein, examples of "stringent conditions" include conditions under which mutually highly homologous nucleotide sequences, for example, nucleotide sequences sharing homology of 80, 90, 95, 97 or 99% or more, hybridize to each other, and under which mutually less homologous nucleotide sequences do not hybridize to each other. Such conditions include, specifically, ordinary Southern hybridization washing conditions, for example, conditions of washing 1 time, or 2 to 3 times, at a salt concentration and temperature equivalent to 60° C., 1×SSC, 0.1% SDS, 0.1×SSC, 0.1% SDS, or even 68° C., 0.1×SSC, 0.1% SDS, and the like.

As a probe, a partial sequence of the nucleotide sequence of SEQ ID NOs: 1, 3, 5, 7, 9 or 11 can also be used. Such a probe can be prepared by PCR with an oligonucleotide prepared on the basis of the nucleotide sequence as the primer, and with a DNA fragment including the nucleotide sequence of SEQ ID NOs: 1, 3, 5, 7, 9 or 11 as the template. For example, when a DNA fragment of about 300 bp long is used as the probe, hybridization washing conditions of 50° C., 2×SSC, 0.1% SDS can be used.

A transglutaminase can be obtained by, for example, subjecting a product expressed and secreted by a microorganism and the like (including the transformants described below) to the steps of separation, recovery, purification and the like. A transglutaminase expressed by a microorganism and the like may also be used.

"Transglutaminase activity" can mean, as stated above, the formation of a cross-linking between a glutamine residue and a lysine residue in a protein. The transglutaminase activity can be measured after the transglutaminase is separated and purified from the host microorganism and the like, and can also be measured while it is being expressed in a microorganism and the like.

Transglutaminase activity can be assayed by the hydroxamate method (J. Biol. Chem., 241, 5518-5525, 1966).

Each activity unit of transglutaminase in the hydroxamate method is defined as follows. Specifically, a reaction can be carried out with benzyloxycarbonyl-L-glutaminylglycine and hydroxylamine as substrates, and the resulting hydroxamic acid is converted to an iron complex in the presence of trichloroacetic acid, after which the amount thereof is measured at an absorbance of 525 nm. A standard curve is thus generated from the amount of hydroxamic acid, and the amount of enzyme that produces 1 μmol of hydroxamate in 1 minute is defined as 1 unit of activity of transglutaminase. Details of this method of measurement have been reported (see, for example, JP-A-SHO-64-27471 and the like).

"WT (wild-type) transglutaminase (TG)" means a naturally occurring transglutaminase not having a mutation introduced into the amino acid sequence thereof.

As mentioned herein, "disulfide bond-introduced transglutaminase (TG)" means a transglutaminase prepared by introducing an amino acid mutation capable of forming a disulfide bond (substitution of any two amino acid residues in mutually appropriate spatial positions to cysteine residues) into the amino acid sequence of a WT transglutaminase (SEQ ID NO:2 and the like). To obtain a transglutaminase mutant protein as described herein, it is convenient that this "disulfide bond-introduced transglutaminase" be modified. This can also be referred to as "the original (or template)" disulfide bond-introduced transglutaminase. The same can also be obtained by modifying a WT transglutaminase.

Examples of such "disulfide bond-introduced transglutaminases" include, but are not limited to, those disclosed in the above-described WO2008/099898; however, a TG with improved heat resistance as compared with WT transglutaminase can be used. Described in detail herein is a step for obtaining a heat-resistant transglutaminase (a transglutaminase mutant) by introducing random mutations into a disulfide bond-introduced mutant which is known to have good heat resistance, for example, wherein the amino acids in the 3-position and 283-position of SEQ ID NO:2 have been substituted with cysteine. However, disulfide bond-introduced TGs other than this, such as mutants having cysteine substitutions at the amino acids in the 3-position and 283-position or the positions corresponding thereto of the above-described SEQ ID NOs: 2, 4, 6, 8, 10 or 12 or homologous thereof may also be used as the template.

Herein, the transglutaminase mutant proteins as described herein have improved heat resistance as compared with the heat resistance of a disulfide bond-introduced transglutaminase.

At some temperatures, the activity of WT transglutaminase is considerably reduced by incubation over a long time. Herein, "improved heat resistance", that is, thermal stability can mean that even within a temperature range that will reduce the activity of WT transglutaminase over a long period of time, for example, about 10 minutes or more, for example, at a temperature of about 50° C. or more, about 55° C. or more, about 60° C. or more, about 65° C. or more, or even about 68° C. or more, the mutated enzyme is able to retain its activity for a longer period of time. Hence, "improved heat resistance" can mean that when a mutated transglutaminase is incubated at a temperature in this range, for example, about 50° C., about 55° C., about 60° C., about 65° C., or about 68° C., for a long time, for example, about 1 hour, about 2 hours, about 3 hours, the ratio of activity reduction of the mutated transglutaminase is smaller than that of WT transglutaminase, or of the original disulfide bond-introduced transglutaminase.

A transglutaminase mutant protein is, for example, a protein that has a residual activity of 1% or more, 3% or more, 10% or more, or even 20% or more, after being heated at 65° C. for 10 minutes.

From the viewpoint of production efficiency, the expression level of the transglutaminase mutant protein as described herein is not remarkably reduced, as compared with the WT transglutaminase or the original disulfide bond-introduced transglutaminase, particularly the original disulfide bond-introduced transglutaminase, when expressed by the method described herein or the like.

The transglutaminase mutant protein as described herein can be a protein having (A) an amino acid sequence having one or more mutations at one or more positions selected from among the 101-position, 157-position and 250-position; or (B) an amino acid sequence having a substitution, deletion, addition and/or insertion of one or several residues at a position other than 101-position, 157-position and 250-position, in SEQ ID NO: 2. Furthermore, proteins having (C) an amino acid sequence having a mutation at one or more positions corresponding to the 101-position, 157-position and 250-position in SEQ ID NO: 2, in an amino acid sequence selected from among SEQ ID NOs: 4, 6, 8, 10 and 12, or in the amino acid sequence of a protein having a homology of 70% or more, 80% or more, 90% or more, 95% or more, or even 98% or more, to an amino acid sequence selected from among SEQ ID NO:2, 4, 6, 8, 10 and 12 and possessing transglutaminase activity; or (D) an amino acid sequence having a substitution, deletion, addition and/or insertion of one or more residues at a position other than the positions corresponding to the 101-position, 157-position and 250-position of SEQ ID NO:2, in the sequence (C), also fall in the scope of the present invention.

Of the above-described proteins, proteins further incorporating one or more amino acid mutations capable of forming a disulfide (S—S) bond also fall in the scope of the present invention. The mutations can include, but are not limited to, those disclosed in WO2008/099898, and can be, for example, substitution of the 3-position and 283-position to cysteine, substitution of the 2-position and 282-position to cysteine, substitution of the 2-position and 283-position to cysteine, or substitution of the 7-position and 58-position to cysteine.

Specifically, the transglutaminase mutant protein described herein can be a protein having (A) an amino acid sequence having mutation to cysteine at the 3-position and 283-position, the 2-position and 282-position, the 2-position and 283-position, or the 7-position and 58-position, and also having a mutation at one or more positions selected from among the 101-position, 157-position and 250-position; or (B) an amino acid sequence having a substitution, deletion, addition and/or insertion of one or several residues at a position corresponding to SEQ ID NO: 2 other than those mentioned in (A) above. Furthermore, proteins having (C) an amino acid sequence having mutations to cysteines at the positions corresponding to positions in SEQ ID NO: 2 of the 3-position and 283-position, the 2-position and 282-position, the 2-position and 283-position, or the 7-position and 58-position, and also having a mutation at one or more positions selected from among the positions corresponding to the 101-position, 157-position or 250-position, of SEQ ID NO:2, in an amino acid sequence selected from among SEQ ID NO: 4, 6, 8, 10 and 12, or an amino acid sequence having mutations to cysteines at the positions corresponding to the 3-position and 283-position, and also having mutation at one or more positions selected from among the positions corresponding to the 101-position, 157-position and 250-position, of SEQ ID NO:2, in the amino acid sequence of a protein having a homology of 70% or more, 80% or more, 90% or more, 95% or more, 98% or more, to an amino acid sequence selected from among SEQ ID NO:2, 4, 6, 8, 10 and 12 and possessing transglutaminase activity; or (D) an amino acid sequence having a substitution, deletion, addition and/or insertion of one or several residues at a position other than the positions mentioned in (C) above, in the sequence (C), also fall in the scope of the present invention.

The amino acid sequence (B) above is specifically an amino acid sequence having, in addition to mutations to cysteines at the 3-position and 283-position, the 2-position and 282-position, the 2-position and 283-position, or the 7-position and 58-position, and mutation at one or more positions selected from among the 101-position, 157-position and 250-position of SEQ ID NO:2, a substitution, deletion, addition and/or insertion of one or several residues in the indicated respective positions and/or at a position other than those listed. The same applies to the amino acid sequence (D) above.

Herein, positions "corresponding to" the aforementioned positions in an amino acid sequence selected from among SEQ ID NOs: 4, 6, 8, 10 and 12 can be determined by aligning these sequences with the amino acid sequence of SEQ ID NO: 2. It is also possible to align the amino acid sequence of a transglutaminase homologue other than any one shown herein with the amino acid sequence of SEQ ID NO: 2 to determine a "corresponding" position, and to introduce a mutation into the position. For example, when a gap is introduced in aligning SEQ ID NO: 2 with another sequence, the possible forward or backward shift of the positions mentioned above should be noted. For corresponding positions, see, for example, FIG. 4 of WO2008/099898.

Algorithms used for alignment of amino acid sequences include NCBI BLAST (National Center for Biotechnology Information Basic Local Alignment Search Tool), the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0, part of the CGC sequence alignment software package)], the algorithm described in Pearson et al., Proc. Natl. Acad. Sci. USA, 85:2444-2448 (1988) [the algorithm is incorporated in the FASTA program in the GCG software package], and the like.

Besides the transglutaminase derived from *Streptomyces mobaraensis* (MTG), it is possible to modify an enzyme possessing transglutaminase activity recognized as having some amino acid sequence homology to this enzyme, or an enzyme possessing transglutaminase activity expected to have a 3D (three-dimensional) structure similar to that of this enzyme, on the basis of the 3D structure of MTG. An amino acid substitution that is effective in modifying the substrate specificity and the like in MTG is expected to be also effective in related enzymes derived from microorganisms such as *Streptomyces cinnamoneus* and *Streptomyces lydicus* (JP-T-HEI-10-504721).

The transglutaminase mutant protein as described herein can have mutations to cysteines in the 3-position and 283-position from among the above-described positions, or positions corresponding thereto, in SEQ ID NO: 2, 4, 6, 8 or 10, including homologous sequences thereof, and including, in addition to the cysteine residues in the 3-position and 283-position, mutations selected from among mutations at the 101-position, including a mutation to proline, mutation at the 157-position, including a mutation to alanine or serine, and mutation at the 250-position, including a mutation to alanine or arginine, or similar mutations at positions corresponding thereto. The mutant protein can have, in addition to these mutations, a substitution, deletion, addition and/or insertion of one or several residues.

The mutant protein can include any combination of the above-described mutations, as long as the transglutaminase mutant protein obtained possesses transglutaminase activity, and in particular has improved heat resistance compared with the original disulfide bond-introduced transglutaminase. The amino acid mutations in the above-described positions can be amino acid substitution mutations.

In addition to these mutations, particularly mutation to cysteine in the above-described 3-position and 283-position, only 1 pair, or a combination of plural pairs, of mutations to cysteine can be present. Such pairs of mutations to cysteine include, but are not limited to, those disclosed in WO2008/099898. Such a protein can be prepared according to methods known in the art.

The above-described substitutions, deletions, additions and/or insertions are not particularly limited, as long as the transglutaminase mutant protein obtained possesses transglutaminase activity, and particularly as long as the heat resistance thereof is improved compared with the original disulfide bond-introduced transglutaminase. Although it is desirable that the number of substitutions, deletions, additions and/or insertions present in the mutant protein be one or several residues, such as 1 to 30, 1 to 15, 1 to 5, 3 or 2 residues, any number of amino acids may be substituted, inserted, added and/or deleted as long as the mutant protein possesses transglutaminase activity, and particularly as long as the heat resistance thereof is improved compared with the original disulfide bond-introduced transglutaminase. For example, when this mutation is a substitution, a substitution with a similar amino acid, such as a conservative amino acid substitution, is known to be unlikely to influence the function of the protein, so a substitution with a similar amino acid can occur. Here, "a similar amino acid" can mean an amino acid having similar physiochemical properties. Examples thereof include amino acids classified in the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Specific examples of conservative amino acid substitutions are known in the technical field.

The transglutaminase mutant protein as described herein can be a protein having a mutation of the aspartic acid at the 3-position to cysteine, mutation of the serine at the 101-position to proline, mutation of the glycine at the 157-position to serine, mutation of the glycine at the 250-position to arginine, and mutation of the glycine at the 283-position to cysteine, all in SEQ ID NO:2.

Also included are proteins having, in addition to the mutations of the aspartic acid at the 3-position to cysteine and mutation of the glycine at the 283-position to cysteine, two mutations selected from among mutations of the serine at the 101-position to proline, mutation of the glycine at the 157-position to serine, and mutation of the glycine at the 250-position to arginine, and also having mutation to another amino acid in the remaining one position, in SEQ ID NO:2. These proteins can include, in addition to mutation of the aspartic acid at the 3-position to cysteine and mutation of the glycine at the 283-position to cysteine, (1) mutation of the serine at the 101-position to proline, mutation of the glycine at the 157-position to serine, and mutation of the glycine at the 250-position to alanine, valine, leucine, methionine, proline, phenylalanine, tryptophan, serine, threonine, asparagine, glutamine, tyrosine, lysine, arginine, histidine or aspartic acid; (2) mutation of the glycine at the 157-position to serine, mutation of the glycine at the 250-position to arginine, and mutation of the serine at the 101-position to glycine, alanine, valine, isoleucine, proline, phenylalanine, asparagine, glutamine, tyrosine, lysine, arginine or glutamic acid; or (3) mutation of the serine at the 101-position to proline, mutation of the glycine at the 250-position to arginine, and mutation of the glycine at the 157-position to alanine, valine, isoleucine, serine, asparagine, lysine, arginine, histidine, aspartic acid or glutamic acid, all in SEQ ID NO:2.

Also included are proteins having, in addition to mutation of the aspartic acid at the 3-position to cysteine and mutation of the glycine at the 283-position to cysteine, mutation of the serine at the 101-position to proline; mutation of the glycine at the 157-position to alanine, serine or arginine; and mutation of the glycine at the 250-position to alanine, phenylalanine, serine, asparagine or arginine, all in SEQ ID NO: 2.

Also included are proteins which include, in addition to mutation of the aspartic acid at the 3-position to cysteine and mutation of the glycine at the 283-position to cysteine, (1) mutation of the serine at the 101-position to proline, mutation of the glycine at the 157-position to serine, and mutation of the glycine at the 250-position to alanine, phenylalanine, serine, asparagine or arginine; (2) mutation of the glycine at the 157-position to serine, mutation of the glycine at the 250-position to arginine, and mutation of the serine at the 101-position to proline; or (3) mutation of the serine at the 101-position to proline, mutation of the glycine at the 250-position to arginine, and mutation of the glycine at the 157-position to alanine, serine or arginine, all in SEQ ID NO:2.

Of the above described proteins, proteins wherein the arginine at the 208-position has further been mutated are also included. Examples include proteins wherein, in addition to mutation of the aspartic acid at the 3-position to cysteine, mutation of the serine at the 101-position to proline, mutation of the glycine at the 157-position to serine, mutation of the glycine at the 250-position to arginine, and mutation of the glycine at the 283-position to cysteine, the arginine at the 208-position has further been mutated, all in SEQ ID NO: 2. For example, this mutation can be a mutation of the arginine at the 208-position to leucine, alanine or glutamic acid.

Alternatively, proteins further including, in addition to mutation of the aspartic acid at the 3-position to cysteine, mutation of the serine at the 101-position to proline, mutation of the glycine at the 157-position to serine, mutation of the glycine at the 250-position to arginine, and mutation of the glycine at the 283-position to cysteine, (1) mutation of the arginine at the 208-position to tryptophan, (2) mutation of the aspartic acid at the 268-position to asparagine, (3) mutation of the valine at the 132-position to leucine, (4) mutation of the arginine at the 238-position to methionine, or (5) mutation of the glutamic acid at the 249-position to lysine, all in SEQ ID NO:2 can also be mentioned.

A polynucleotide that encodes the transglutaminase mutant proteins as described herein is also provided. Such a polynucleotide can be acquired using methods known in the art, for example, a method described herein. This polynucleotide can be inserted into a vector using an appropriate restriction enzyme to obtain a recombinant vector.

A vector backbone used as a recombinant vector can be chosen as appropriate according to the purpose thereof, for example, cloning, protein expression, or from among ones suitable for the chosen host cell, usually a microorganism, into which this vector is to be introduced. When this recombinant vector is an expression vector, this expression vector includes a polynucleotide as described herein operably linked to an appropriate promoter, and can also include a transcription termination signal, for example a terminator region, downstream of a polynucleotide as described herein. Furthermore, the recombinant vector can further include a selection marker gene, such as drug resistance genes, genes that compensate for an auxotrophic mutation and the like, which are useful for selecting a transformant. The recombinant vector may also include a sequence that encodes a tag sequence, which can be useful for the separation/purification of the expressed protein, and the like. The vector can also be one that can be integrated into the genome of the chosen host cell.

The vector can be introduced into the chosen host cell using, for example, a known transformation technology such as the competent cell method, protoplast method, calcium phosphate co-precipitation method, polyethylene glycol method, lithium method, electroporation method, microinjection method, liposome fusion method, or particle gun method.

A host cell transformed with such a recombinant vector is also provided (hereinafter, also referred to as a transformant). As host cells, prokaryotic cells such as *Escherichia coli* and actinomycetes, and eukaryotic cells such as yeast can be mentioned. If the expression of a protein is desired, the host cell can be one suitable for protein production, and capable of expressing the mutant protein as described herein in a functional form. The transformant can be obtained using one of the transformation technologies mentioned above. Although any microorganism for which a usable recombinant vector system has been developed can be utilized as a host cell; host cells can include, but are not limited to, *E. coli, Corynebacterium glutamicum*, yeast, bacteria of the genus *Bacillus*, various actinomycetes and the like.

The transformant can be cultured under conditions in common use in the art. For example, culturing temperature, time, medium composition, pH, stirring conditions and the like can be selected as appropriate according to the transformant cultured.

The transglutaminase mutant protein as described herein can be expressed by the transformant as described herein. The transglutaminase mutant protein can be used after being secreted from the transformant or separated/purified from the transformant, and can also be used while still contained within the transformant. Separation and purification of the protein can be performed according to a known method.

The transglutaminase mutant protein can be first expressed as a pro-form, and then treated with an appropriate protease, such as subtilisin, to yield the mature form; alternatively, the pro-form and a protease may be expressed at the same time in the chosen host cell to obtain a mature form.

The transglutaminase mutant protein with improved heat resistance as compared with the original disulfide bond-introduced transglutaminase as described herein can be provided by introducing random mutations into the disulfide bond-introduced transglutaminase gene in order to further improve the heat resistance of the disulfide bond-introduced transglutaminase.

Introduction of random mutations into the disulfide bond-introduced transglutaminase gene and primary screening for the disulfide bond-introduced transglutaminase mutants can be achieved as described below. The sequence of the transglutaminase gene derived from the *S. mobaraense* DSMZ strain has already been determined (Eur. J. Biochem., 257, 570-576, 1998). With reference to this sequence, a mutated transglutaminase gene can be constructed wherein substitution of the 7-position and 58-position to cysteine, or substitution of the 2-position and 282-position to cysteine, or substitution of the 2-position and 283-position to cysteine, or substitution of the 3-position and 283-position to cysteine can be introduced into the mature form region that encodes the MTG activity itself, which is about 1,000 bp. Mutations can be introduced into this disulfide bond-introduced transglutaminase gene, so that the mutations will be introduced into two or three sites at the base sequence level. By treating the PCR product with the mutations and the MTG expression vector pPSPTG11 (App. Env. Micro., 2003, 69, 358-366) with restriction endonucleases and ligating them, the MTG gene portion of pPSPTG11 can easily be replaced with the mutated MTG gene. *E. coli* is transformed with the plasmid prepared by the ligation, and the colony obtained is subjected to mixed culture, followed by plasmid extraction. YDK010 constructed from *Corynebacterium glutamicum* AJ12036 (FERM BP-734) (WO 2002/081694) (the method of construction used is described in WO2002/081694) is transformed with the obtained plasmid by electroporation.

The transformants can be screened by the hydroxymate method (J. Biol. Chem., 241, 5518-5525, 1966). The assay can be performed using either a 96-well well plate or a test tube. When a strain without the mutations is used as the control, a mutated protein having an absorbance equivalent to or more than that of the control can be selected.

Mutation points can be analyzed by confirming the base sequences of the strains obtained by the screening. For ones whose mutation points have been identified, the specific activity can be calculated by measuring the activity and protein content. The activity and protein content can be measured by methods described in the literature (Prot. Exp. Puri., 2002, 26, 329-335).

If a mutant having a plurality of mutations is found after identifying mutation sites that has high activity by confirming the base sequence, it is also possible to generate a mutant incorporating only one mutation point, and accurately evaluate the effect of the mutation point on the activity. It is also possible to generate a protein with multiple mutations by selecting a plurality from among identified mutation sites, and evaluate the effects of combinations of mutation points. Introduction of mutations can be conveniently achieved using the QuikChange II Site-Directed Mutagenesis Kit of Stratagene and the like.

Cultivation of the transformant obtained, and separation and purification of the transglutaminase mutant protein can be performed as, for example, described below. A CM2G medium containing kanamycin is dispensed to test tubes. The transformant is inoculated and pre-cultured at 30° C. for 24 hours. An MM medium containing both kanamycin and $CaCO_3$ is dispensed to Sakaguchi flasks at 50 ml per flask, and the pre-culture broth is inoculated and cultured. After the culture broth is centrifuged, the supernatant is filtered, and passed through Sephadex G25(M) to replace the solvent with 20 mM phosphate buffer solution, pH 7.0. Subtilisin is added in an amount 1/100 that of transglutaminase, and the reaction is allowed to proceed at 30° C. for 16 hours to activate the transglutaminase. The activated solution is exchanged with an equilibration buffer solution for cation exchange chromatography (20 mM acetate buffer solution, pH 5.5) using Sephadex G25(M). Next, the entire amount is loaded onto a cation exchange column (Resource S 6 ml; manufactured by GE Healthcare Bioscience) fully equilibrated with the same buffer solution. After re-equilibration with the same buffer solution, a protein fraction eluted at a NaCl concentration of nearly 200 mM on a linear concentration gradient of 0→0.5 M NaCl is fractionated with UV absorption at a wavelength of 280 nm as an index. The activities and protein contents of the resulting fractions are measured, and fractions with nearly the same specific activity in the vicinity of the peak top, excluding fractions of low specific activity, are recovered. The recovered fractions are passed through Sephadex G25(M) to replace the solvent with 20 mM phosphate buffer solution, pH 6.0. The samples obtained are diluted to a concentration of about 1 mg/ml with 20 mM phosphate buffer solution, pH 6.0, and stored at −80° C. until use.

A method of processing a substrate protein using the transglutaminase mutant protein as described herein, or a transformant expressing the protein, is also provided. Proteins having a glutamine residue and/or lysine residues which can be accessed by the transglutaminase are considered capable of being a substrate for the transglutaminase. This method is applicable to protein cross-linking reaction at a temperature range that is typically inappropriate for the WT transglutaminase or conventional disulfide bond-introduced transglutaminase, and so can be used in textile processing, tanning and the like.

For example, the mutant protein can be used in a reaction carried out at about 40° C. to about 100° C., about 50° C. to about 100° C., about 55° C. to about 100° C., about 60° C. to about 100° C., or even about 65° C. to about 100° C. In particular, because the high temperature used in textile processing is at least about 60° C., the mutant protein as described herein is suitable for use in textile processing.

EXAMPLES

The present invention is hereinafter described more specifically by means of the following non-limiting examples.

Example 1

Introduction of Random Mutations into a Gene Encoding a Transglutaminase into which Disulfide Bond(s) have been Introduced, and Construction of a Screening Library of these Transglutaminase Mutants The MTG gene consists of three regions: a pre-region, a pro-region, and a mature form region. Mutations were introduced into the mature form region that encodes the MTG activity itself (about 1000 bp), which incorporates the D3C and G283C mutations which had been introduced to form a disulfide bond (D3C/G283C), by error-prone PCR. The sequence of the transglutaminase gene derived from the *S. mobaraense* DSMZ strain has already been determined (Eur. J. Biochem., 257, 570-576, 1998). With reference to this sequence, a Forward primer (TCCATAGCAATCCAAAGG (SEQ ID NO:13)) and a Reverse primer (GGGCGAC-CGAGAAGTTTTTTACAAAAGGCA (SEQ ID NO:14)) were synthesized upstream and downstream, respectively, of the mature form region; error-prone PCR was performed with the reaction liquid composition and the conditions shown below, using the Genemorph Ver. 2 kit (manufactured by STRATAGENE), according to the procedure recommended by the manufacturer. The reaction liquid composition was set so that the mutations would be introduced in two or three sites at the base sequence level. To replace the corresponding portion of the pro-MTG expression vector pPSPTG11 described in Appl. Environ. Microbiol., 2003, 69(1), 358-366 with the PCR product obtained, they were treated with BamHI (37° C., 2 hours), and then treated with EcoO65I (37° C., 2 hours). The vector was cut out and dissolved in 60 μl of ddH$_2$O. The PCR product was purified by ethanol precipitation. After the vector and the PCR product were mixed together to reach a ratio of 1:5, and they were ligated by allowing a reaction to proceed at 16° C. for 3 hours using Ligation Solution Kit I (manufactured by Takara Inc.). *E. coli* JM109 was transformed with the plasmid prepared by the ligation to yield 4500 colonies, which were subjected to plasmid extraction in sets of 500 colonies. YDK010 constructed from *Corynebacterium glutamicum* AJ12036 (FERM BP-734) (WO 2002/081694) (the method of construction used is described in WO 2002/081694) was transformed with the plasmid obtained by the extraction by electroporation; the transformant was cultured (30° C., 24 hours) in a CM2G plate (Glucose 5 g, Polypepton 10 g, Yeast extract 10 g, NaCl 5 g, DL-Met 0.2 g, pH 7.2/1 L) supplemented with 25 μg/ml kanamycin. The electroporation was performed by the method described in the literature (FEMS Microbiol. Lett., 53, 299-303, 1989).

Example 2

Primary Screening of Transglutaminase Mutants into which a Disulfide Bond was Introduced 1 ml of a CM2G medium (Glucose 5 g, Polypepton 10 g, Yeast extract 10 g, NaCl 5 g, DL-Met 0.2 g, pH 7.2/1 L) supplemented with 25 μg/ml kanamycin was dispensed to each 96-well deep well. Each of the transformants obtained in Example 1 (about 10000 strains) was inoculated and precultured at 1,500 rpm, 30° C. for 24 hours. 1 ml of an MM medium (Glucose 60 g, MgSO$_4$7H$_2$O 1 g, FeSO$_4$7H$_2$O 0.01 g, MnSO$_4$5H$_2$O 0.01 g, (NH$_4$)$_2$SO$_4$ 30 g, KH$_2$PO$_4$ 1.5 g, VB1-HCl 0.45 mg, Biotin 0.45 mg, DL-Met 0.15 g, pH 7.5/1 L) supplemented with 25 μg/ml kanamycin and 50 g/L CaCO$_3$ was dispensed to each 96-well deep well, and 50 μl of the preculture broth was subcultured. After cultivation at 1,500 rpm, 30° C. for 5 hours, DTT was added to the 96-well deep well to reach a concentration of 3 mM. After the addition of the DTT, each transformant was cultured at 1500 rpm, 30° C. for 43 hours. The culture broth was centrifuged at 3000 rpm, 4° C. for 10 minutes; 200 μL of the culture supernatant obtained was diluted 5 fold with 20 mM MOPS, pH 7. Subtilisin in an amount 1/100 that of MTG was added to the dilution, and a reaction was allowed to proceed at 30° C. for 16 hours to activate the MTG. Screening was performed by measuring the activity by the hydroxamate method. In the measurement of the activity, 30 μl of the activated solution was dispensed to a 96-well well and warmed at 37° C. for 5 minutes in advance. 50 μl of liquid A (0.05 M MES, 0.1M NH$_2$OH, 0.03 M CBZ-Gln-Gly, pH 6.0), previously warmed at 37° C. for 5 minutes, was dispensed to each well, and a reaction was allowed to proceed at 37° C. for 20 minutes, after which 50 μl of liquid B (1N HCl, 4% TCA, 1.67% FeCl$_3$.6H$_2$O) was dispensed to each well to stop the reaction, after which absorbance at 525 nm was measured using a plate reader. Next, 100 μL of the reaction liquid was dispensed to each 96-well deep well; PMSF was added to reach 1 mM, and a reaction was allowed to proceed at 25° C. for 1 hour. The PMSF-treated reaction liquid was heated at 65° C. for 10 minutes, using a thermal cycler. The heat-treated reaction liquid was subjected to the hydroxamate method to measure the activity as described above. With the original disulfide bond-introduced transglutaminase mutant (that is, a strain incorporating the D3C and G283C mutations) as the control, 70 strains whose absorbances before and after the heat treatment were nearly equivalent to those of the control and whose residual activities derived from the absorbances before and after the heat treatment were equivalent to or more than those of the control were selected. Hereinafter, the strain incorporating the D3C and G283C mutations and the disulfide bond-introduced transglutaminase (protein) obtained from the strain are also referred to as D3C/G283C, 3/283 or 3-283 for the sake of convenience.

Example 3

Mutation Point Analysis of Strains Selected by Primary Screening

Mutation sites were analyzed by identifying the base sequences of the strains obtained by screening. Each strain obtained by the screening was cultured using a CM2G medium supplemented with 25 μg/ml kanamycin at 30° C. for 24 hours, after which the plasmid was extracted using the QIAprepSpin Miniprep Kit of QIAGEN, and the *E. coli* JM109 strain was transformed therewith. The transformed *E. coli* JM109 strain was cultured with LB medium at 37° C. for 16 hours, after which the plasmid was extracted in the same way. Base sequence analysis was performed, using the ABI PRISM Cycle Sequencing Kit according to the procedure recommended by the manufacturer. As a result, the presence of a mutation point was confirmed in 47 strains, and 30 kinds of mutants were identified (Table 2).

TABLE 2

Table 2 Mutants identified by primary screening

| No. | | Amino acid substitution |
|---|---|---|
| 1 | 1-2-11G | A267V |
| 2 | 1-5-8G | G286C, V326A |
| 3 | 1-6-6D | T263K |
| 4 | 1-7-6B | R48M, Q74E, R100Q, R105W |
| 5 | 2-7-9C | V132I, D237N |
| 6 | 3-2-7D | W272G |
| 7 | 3-6-3B | S246I, D268N |
| 8 | 3-6-5D | Q51L, N196S |
| 9 | 3-6-6A | P99L, A145G, T245A |
| 10 | 3-6-9D | T68I, Y75H, R79I |
| 11 | 3-8-4H | R26S, R238M, S243N |
| 12 | 4-3-11H | S101P |
| 13 | 4-4-9H | T53S, G157S |
| 14 | 5-2-8B | G157A |
| 15 | 5-5-12E | N92S, G250R |
| 16 | 5-6-8H | G250E |
| 17 | 5-7-7D | G250A |
| 18 | 6-3-10E | N92D, G250R |
| 19 | 6-4-9A | T53S |
| 20 | 6-8-5C | N297K |
| 21 | 7-4-5C | Q50H |
| 22 | 7-4-7H | L94M |
| 23 | 7-10-12H | F202L |
| 24 | 8-5-4C | D213Y, R215M |
| 25 | 8-7-8E | L94H, G205R, S246I |
| 26 | 8-8-5C | M16L, S179Y |
| 27 | 9-3-11D | A83T |
| 28 | 10-5-3F | S43N, K194R |
| 29 | 10-5-4A | V112I, G250R |
| 30 | 10-5-8G | R79S |

Example 4

Secondary Screening of Transglutaminase Mutants into which a Disulfide Bond was Introduced 3 ml of a CM2G medium supplemented with 25 μg/ml kanamycin was dispensed to each test tube. Each of the 30 kinds of mutants selected by the primary screening was inoculated and precultured at 30° C. for 24 hours. 4 ml of an MM medium supplemented with 25 μg/ml kanamycin and 50 g/L CaCO₃ was dispensed to each test tube, and 50 μl of the preculture broth was subcultured. After cultivation at 30° C. for 5 hours, DTT was added to reach a concentration of 3 mM. After the addition of the DTT, each mutant was cultured at 30° C. for 43 hours. The culture broth was centrifuged (10,000 rpm, 10 minutes); subtilisin in an amount 1/100 that of MTG was added to the culture supernatant obtained, and a reaction was allowed to proceed at 30° C. for 16 hours to activate the MTG. The activated solution was treated using PD-10 (manufactured by GE Healthcare Bioscience) to exchange the solvent with 20 mM MES, pH 6.0. The culture broth was diluted as appropriate, and secondary screening was performed in the same manner as Example 2. As a result of a measurement of the hydroxamate activity after heat treatment, 7 kinds of mutants (Table 3) exhibited residual activity equivalent to or more than that of the control 3-283.

TABLE 3

Table 3 Mutants selected by secondary screening

|  | Amino acid substitution |
|---|---|
| 4-3-11H | S101→P |
| 4-4-9H | T53→S, G157→S |
| 5-2-8B | G157→A |
| 5-5-12E | N92→S, G250→R |
| 5-7-7D | G250→A |
| 9-3-11D | A83→T |
| 10-5-4A | V112→I, G250→R |

Example 5

Purification of Transglutaminase Enzymes into which a Disulfide Bond was Introduced Selected by Secondary Screening 3 ml of a CM2G medium supplemented with 25 μg/ml kanamycin was dispensed to each test tube. Each of the 7 kinds of mutants selected by the secondary screening and the control (3-283) was inoculated and precultured at 30° C. for 24 hours. 50 ml of an MM medium supplemented with 25 μg/ml kanamycin and 50 g/L CaCO₃ was dispensed to each Sakaguchi flask, and 2.5 ml of the preculture broth was inoculated and cultured at 30° C. for 48 hours. After cultivation at 30° C. for 5 hours, DTT was added to reach a concentration of 3 mM. After the addition of the DTT, each mutant was cultured at 30° C. for 43 hours. The culture broth was centrifuged (8,000 rpm, 10 minutes); subtilisin in an amount 1/100 that of MTG was added to the culture supernatant obtained, and a reaction was allowed to proceed at 30° C. for 16 hours to activate the MTG. The activated solution was exchanged with a cation exchange chromatography equilibration buffer solution (20 mM acetate buffer solution, pH 5.5) using Sephadex G25(M). Next, the entire volume was applied to a cation exchange column (Resource S 6 ml; manufactured by GE Healthcare Bioscience) fully equilibrated with the same buffer solution. After re-equilibration with the same buffer solution, a protein fraction eluted at an NaCl concentration of nearly 200 mM on a linear density gradient of 0→0.5M NaCl was fractionated with UV absorption at a wavelength of 280 nm as an index. The fraction activity and protein content were measured by the above-described methods, and fractions near the peak top with nearly equivalent specific activity, excluding fractions of low specific activity, were recovered. The fractions recovered were passed through Sephadex G25(M) to replace the solvent with 20 mM phosphate buffer solution, pH 6.0. In all cases, chromatography was performed at room temperature.

Example 6

Evaluation of Heat Resistance of the Purified Mutated Enzymes

Each of 8 kinds of purified mutated enzymes was prepared to reach 0.5 mg/mL. 100 μL of the enzyme solution was dispensed to each 96-well deep well; PMSF was added to reach 1 mM, and a reaction was allowed to proceed at 25° C. for 1 hour. The enzyme solutions were heated at 63° C., 64.8° C., 66.6° C., and 68.4° C., each for 10 minutes, using a thermal cycler. 30 μl of each of the non-heated enzyme solution and the enzyme solution heat-treated above was dispensed to each 96-well well and warmed at 37° C. for 5 minutes in advance. 50 μl of liquid A (0.05 M MES, 0.1 M NH₂OH, 0.03 M CBZ-Gln-Gly, pH 6.0), previously warmed at 37° C. for 5 minutes, was dispensed to each well, and a reaction was allowed to proceed at 37° C. for 20 minutes, after which 50 μl of liquid B (1N HCl, 4% TCA, 1.67% FeCl₃6H₂O) was dispensed to each well to stop the reaction, after which absorbance at 525 nm was measured using a plate reader. Taking the absorbance value of the non-heated enzyme solution as 100%, residual activities at 63° C., 64.8° C., 66.6° C., and 68.4° C. were calculated.

The results of the heat resistance evaluation are summarized in Table 4. It was found that all the 7 kinds of mutants exhibited improved heat resistance under the 66.6° C. conditions.

TABLE 4

Table 4 Evaluation of heat resistances of purified mutated enzymes

|  | 25° C. | 63.0° C. | 64.8° C. | 66.6° C. | 68.4° C. |
|---|---|---|---|---|---|
| 3-283 | 100% | 71% | 61% | 32% | 11% |
| 4-3-11H | 100% | 67% | 68% | 54% | 18% |
| 4-4-9H | 100% | 71% | 63% | 41% | 13% |
| 5-2-8B | 100% | 73% | 69% | 44% | 17% |
| 5-5-12E | 100% | 69% | 61% | 42% | 8% |
| 5-7-7D | 100% | 66% | 60% | 39% | 9% |
| 9-3-11D | 100% | 67% | 64% | 49% | 24% |
| 10-5-4A | 100% | 67% | 63% | 49% | 27% |

Example 7

Combinations of Promising Mutation Points

As a result of screening, 7 kinds of mutants were selected, and 7 mutation sites were identified. In order to further improve the heat resistance by combining them, multiple mutants were constructed. Mutations were introduced into 4-3-11H (MSS2 in Table 5) identified in Example 3, using the QuikChange II Site-Directed Mutagenesis Kit of Stratagene, as in Example 1. Introduction of the mutations was checked by analyzing the base sequence in the same manner as the above-described method. The constructed mutants are listed in Table 5.

TABLE 5

Table 5 Combinations of promising mutation points

| No. | | Mutation points introduced |
|---|---|---|
| 1 | 3-283 | |
| 2 | MSS2 | S101P |
| 3 | MSS2α | S101P/G250A |
| 4 | MSS2αA | S101P/G250A/G157A |
| 5 | MSS2αA + 1 | S101P/G250A/G157A/T53S |
| 6 | MSS2αA + 2 | S101P/G250A/G157A/T53S/A83T |
| 7 | MSS2αA + 3 | S101P/G250A/G157A/T53S/A83T/N92S |
| 8 | MSS2αA + 4 | S101P/G250A/G157A/T53S/A83T/N92S/V112I |
| 9 | MSS2αB | S101P/G250A/G157S |
| 10 | MSS2αB + 1 | S101P/G250A/G157S/T53S |
| 11 | MSS2αB + 2 | S101P/G250A/G157S/T53S/A83T |
| 12 | MSS2αB + 3 | S101P/G250A/G157S/T53S/A83T/N92S |
| 13 | MSS2αB + 4 | S101P/G250A/G157S/T53S/A83T/N92S/V112I |
| 14 | MSS2β | S101P/G250R |
| 15 | MSS2βA | S101P/G250R/G157A |
| 16 | MSS2βA + 1 | S101P/G250R/G157A/T53S |
| 17 | MSS2βA + 2 | S101P/G250R/G157A/T53S/A83T |
| 18 | MSS2βA + 3 | S101P/G250R/G157A/T53S/A83T/N92S |
| 19 | MSS2βA + 4 | S101P/G250R/G157A/T53S/A83T/N92S/V112I |
| 20 | MSS2βB | S101P/G250R/G157S |
| 21 | MSS2βB + 1 | S101P/G250R/G157S/T53S |
| 22 | MSS2βB + 2 | S101P/G250R/G157S/T53S/A83T |
| 23 | MSS2βB + 3 | S101P/G250R/G157S/T53S/A83T/N92S |
| 24 | MSS2βB + 4 | S101P/G250R/G157S/T53S/A83T/N92S/V112I |

Example 8

Selection of Promising Multiple Mutants

Each of the plasmids constructed in Example 7 was introduced into *Corynebacterium* by electroporation to yield transformants. 1 ml of a CM2G medium (Glucose 5 g, Polypepton 10 g, Yeast extract 10 g, NaCl 5 g, DL-Met 0.2 g, pH 7.2/1 L) supplemented with 25 μg/ml kanamycin was dispensed to each 96-well deep well. Each transformant was inoculated and precultured at 1,500 rpm, 30° C. for 24 hours. 1 ml of an MM medium (Glucose 60 g, MgSO$_4$7H$_2$O 1 g, FeSO$_4$7H$_2$O 0.01 g, MnSO$_4$5H$_2$O 0.01 g, (NH$_4$)$_2$SO$_4$ 30 g, KH$_2$PO$_4$ 1.5 g, VB1-HCl 0.45 mg, Biotin 0.45 mg, DL-Met 0.15 g, pH 7.5/1 L) supplemented with 25 μg/ml kanamycin and 50 g/L CaCO$_3$ was dispensed to each 96-well deep well, and 50 μl of the preculture broth was inoculated. After cultivation at 1,500 rpm, 30° C. for 5 hours, DTT was added to the 96-well deep well to reach a concentration of 3 mM. After the addition of the DTT, the transformant was cultured at 1500 rpm, 30° C. for 43 hours. The culture broth was centrifuged at 3000 rpm, 4° C. for 10 minutes, and 200 μL of the culture supernatant obtained was diluted 5 fold with 20 mM MOPS, pH 7. Subtilisin in an amount 1/100 that of each TG was added to the dilution, and a reaction was allowed to proceed at 30° C. for 16 hours to activate each TG. Screening was performed by measuring the activity by the hydroxamate method. In the measurement of the activity, 30 μl of the activated solution was dispensed to a 96-well well and warmed at 37° C. for 5 minutes in advance. 50 μl of liquid A (0.05 M MES, 0.1 M NH$_2$OH, 0.03M CBZ-Gln-Gly, pH 6.0), previously warmed at 37° C. for 5 minutes, was dispensed to each well, and a reaction was allowed to proceed at 37° C. for 20 minutes, after which 50 μl of liquid B (1N HCl, 4% TCA, 1.67% FeCl$_3$ 6H$_2$O) was dispensed to each well to stop the reaction, after which absorbance at 525 nm was measured using a plate reader. Next, 100 μL of the reaction liquid was dispensed to a 96-well deep well; PMSF was added to reach 1 mM, and a reaction was allowed to proceed at 25° C. for 1 hour. The PMSF-treated reaction liquid was heated at 67° C. for 10 minutes, using a thermal cycler. The heat-treated reaction liquid was subjected to the hydroxamate method to measure the activity as described above. As a result, 6 kinds of mutants having enzyme activity and expression levels equivalent to or more than those of the control (3-283), and significantly improved residual activity as compared to that of the control were identified (MSS2αA, MSS2αB, MSS2β, MSS2βA, MSS2βA+1 and MSS2βB) (Table 5, FIG. 1).

Example 9

Purification of Promising Multiple Mutants and Evaluation of their Heat Resistance 3 ml of a CM2G medium supplemented with 25 μg/ml kanamycin was dispensed to each test tube. Each of the 6 kinds of mutants identified in Example 8 was inoculated and precultured at 30° C. for 24 hours. 50 ml of an MM medium supplemented with 25 μg/ml kanamycin and 50 g/L CaCO$_3$ was dispensed to each Sakaguchi flask, and 2.5 ml of the preculture broth was subcultured. After cultivation at 30° C. for 5 hours, DTT was added to reach a concentration of 3 mM. After the addition of the DTT, each mutant was cultured at 30° C. for 43 hours. The culture broth was centrifuged (8,000 rpm, 10 minutes); subtilisin in an amount 1/100 that of MTG was added to the culture supernatant obtained, and a reaction was allowed to proceed at 30° C. for 16 hours to activate the MTG. The activated solution was exchanged with a cation exchange chromatography equilibration buffer solution (20 mM acetate buffer solution, pH 5.5) using Sephadex G25(M). Next, the entire volume was applied to a cation exchange column (Resource S 6 ml; manufactured by GE Healthcare Bioscience) fully equilibrated with the same buffer solution. After re-equilibration with the same buffer solution, a protein fraction eluted at an NaCl concentration of nearly 200 mM on a linear density gradient of 0→0.5 M NaCl was fractionated with UV absorption at a wavelength of 280 nm as an index. The activity and protein content of the fraction were measured by the above-described methods, and fractions near the peak top with nearly equivalent specific activity, excluding fractions of low specific activity, were recovered. The fractions recovered were passed through Sephadex G25(M) to replace the solvent with 20 mM phosphate buffer solution, pH 6.0. In all cases, chromatography was performed at room temperature. Each of the 6 kinds of purified mutated enzymes were prepared to reach 0.5 mg/mL. 100 μL of the enzyme solution was dispensed to a 96-well deep well; PMSF was added to reach 1 mM, and a reaction was allowed to proceed at 25° C. for 1 hour. The enzyme solutions were heated at 63.6° C., 64.2° C., 66.8° C., 68.2° C., 69.7° C., and 71.1° C., each for 10 minutes, using a thermal cycler. 30 μl of each of the non-heated enzyme solution and the heat-treated enzyme solution was dispensed to a 96-well well and warmed at 37° C. for 5 minutes in advance. 50 μL of liquid A (0.05 M MES, 0.1 M NH$_2$OH, 0.03 M CBZ-Gln-Gly, pH 6.0), previously warmed at 37° C. for 5 minutes, was dispensed to each well, and a reaction was allowed to proceed at 37° C. for 20 minutes, after which 50 μl of liquid B (1N HCl, 4% TCA, 1.67% FeCl$_3$ 6H$_2$O) was dispensed to each well to stop the reaction, after which absorbance at 525 nm was measured using a plate reader. Taking the absorbance value of the non-heated enzyme solution as 100%, residual activities at 63.6° C., 64.2° C., 66.8° C., 68.2° C., 69.7° C., and 71.1° C. were calculated.

Figure 2:
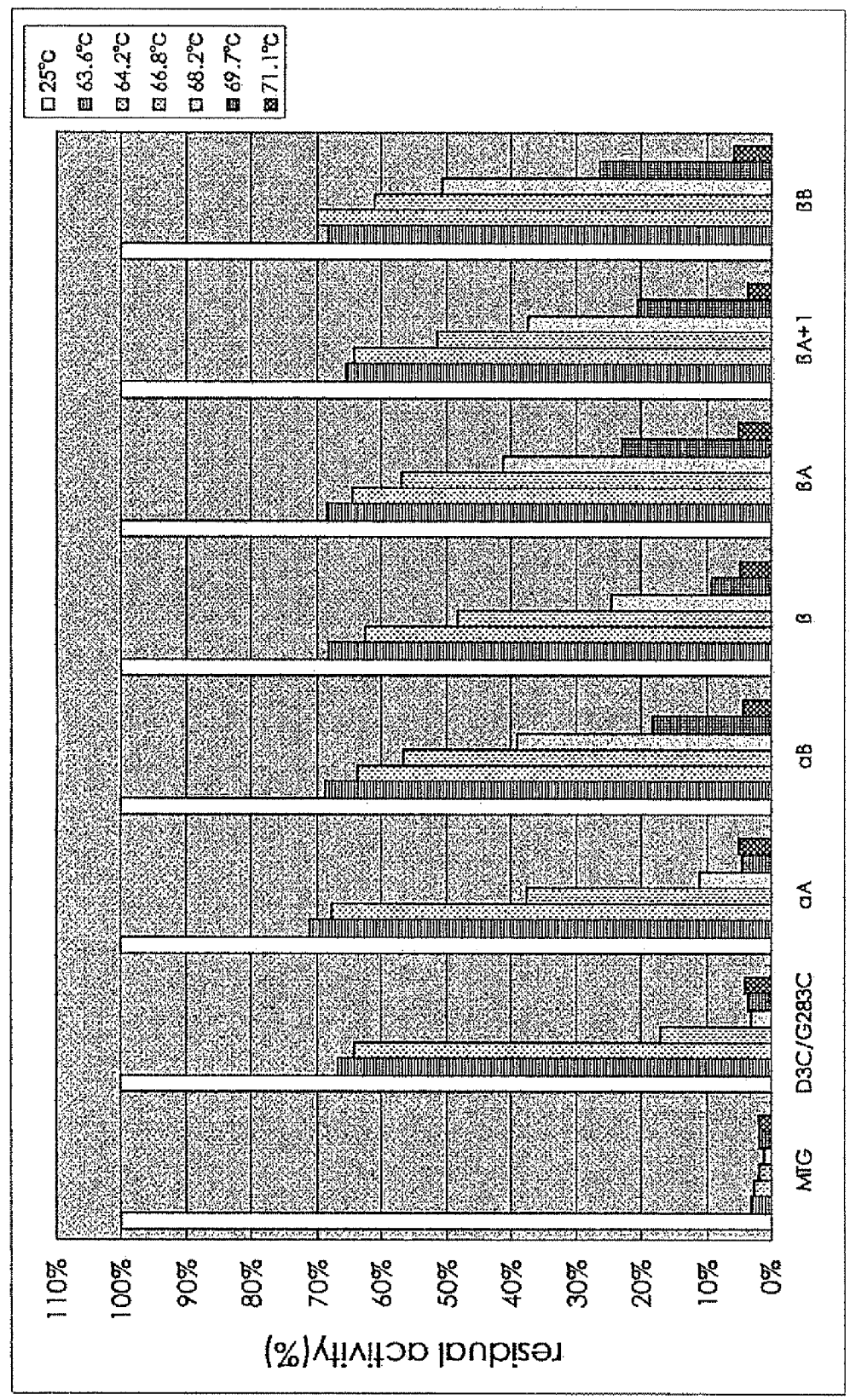
FIG. 2 is a graphic representation showing the heat resistances (residual activities) of the 6 mutants identified in Example 8.

The results of the heat resistance evaluation are summarized in FIG. 2. It was observed that when heat-treated at 68.2° C. for 10 minutes, the control parent enzyme lost its activity, whereas all the 6 kinds of αA, αB, β, βA, βA+1, and βB had a significantly improved heat resistance.

Example 10

Evaluation of Heat Resistance of MSS2βB by the Hydroxamate Method

Using MSS2βB (S101→P, G157→S, G250→R) purified according to the method described in Example 9, D3C/G283C, and wild-type MTG (in this Example, hereinafter simply referred to as MTG), the temperature dependence of the activity was measured by the hydroxamate method. Enzyme concentrations were determined by reversed phase chromatography according to the method described in Protein Expr. Purif. 26 (2002) 329-335. 1.0 mL of liquid A (0.05 M MES, 0.1 M $NH_2OH$, 0.03 M CBZ-Gln-Gly, pH 6.0), previously warmed at 35° C., 45° C., 50° C., 55° C., 60° C., 65° C., and 70° C. for 5 minutes, was dispensed to each test tube; 100 μL of the enzyme solution was added, and a reaction was allowed to proceed at each temperature for 10 minutes, after which 1.0 mL of liquid B (1N HCl, 4% TCA, 1.67% $FeCl_3$ $6H_2O$) was dispensed to stop the reaction, after which absorbance at 525 nm was measured. Specific activities were calculated according to the method described in Protein Expr. Purif. 26 (2002) 329-335.

Figure 3:
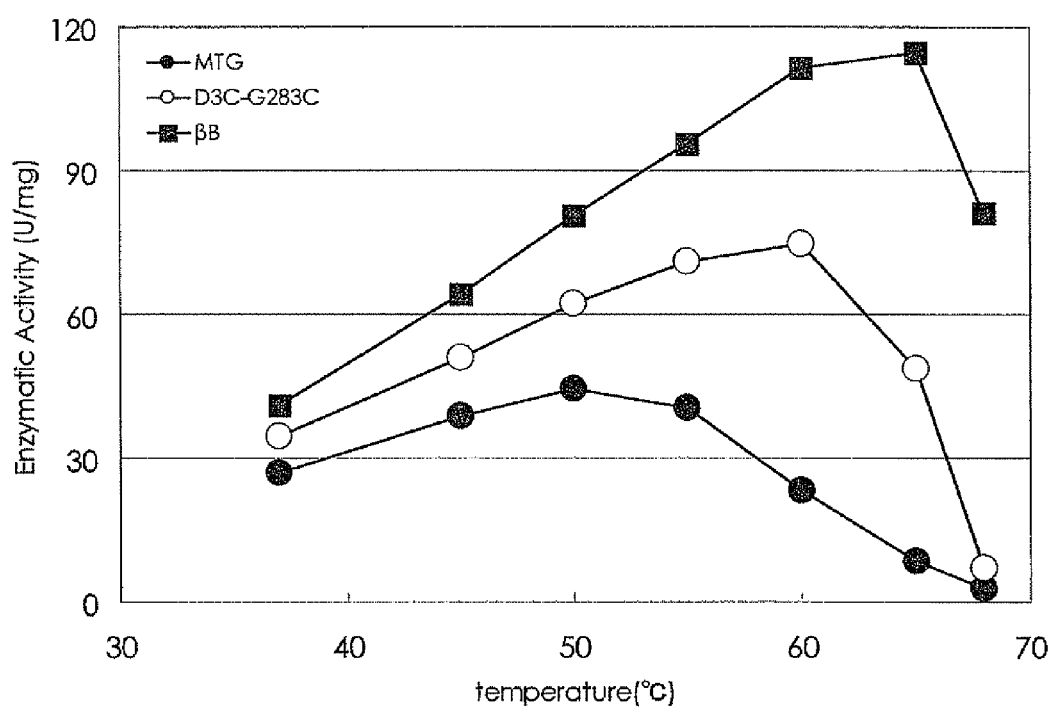
FIG. 3 is a drawing showing the results of the heat resistance evaluation in Example 10.

The results of the heat resistance evaluation are summarized in FIG. 3. MTG exhibited a maximum activity at 45° C. to 50° C. with a specific activity of about 45 U/mg. D3C/G283C exhibited a maximum activity at 55° C. to 60° C. with a specific activity of about 75 U/mg; its heat resistance exceeded that of MTG by 10° C., and its specific activity doubled that of MTG. MSS2βB (S101→P, G157→S, G250→R) exhibited a maximum activity at 60° C. to 65° C. with a specific activity of about 115 U/mg; its heat resistance exceeded that of D3C/G283C by 5° C., and the maximum value of its specific activity improved by about 50% that of D3C/G283C.

Example 11

Confirmation of the Improved Heat Resistance with the Introduction of Mutation Points As a result of the above-described experiment, it was observed that MSS2βB (S101→P, G157→S, G250→R) had improved heat resistance compared with D3C/G283C. To confirm that the sites of introduction of the mutation points S101→P, G157→S, and G250→R into D3C/G283C contribute to the improvement in the heat resistance, verification by amino acid substitutions was performed. Specifically, a mutant generated by introducing the amino acid substitution S101→G, A, V, I, P, F, N, Q, Y, K, R or E into D3C/G283C and incorporating G157→S and G250→R, a mutant generated by introducing the amino acid substitution G157→A, V, I, S, N, K, R, H, D or E into D3C/G283C and incorporating S101→P and G250→R, and a mutant generated by introducing the amino acid substitution G250→A, V, L, M, P, F, W, S, T, N, Q, Y, K, R, H or D into D3C/G283C and incorporating S101→P and G157→S were constructed. Mutations for achieving the amino acid substitutions were introduced into MSS2βB identified in Example 7, using the QuikChange II Site-Directed Mutagenesis Kit of Stratagene, as in Example 1. Introduction of the mutations was checked by analyzing the base sequence in the same manner as the above-described method. The constructed mutants are listed in Table 6. Each constructed plasmid was introduced into *Corynebacterium* by electroporation to yield transformants.

TABLE 6

Table 6 Combinations of promising mutation points

| No. | Mutation points introduced into natural-type MTG | Amino acid substitution |
|---|---|---|
| 1 | D3C/G157S/G250R/G283C | S101G |
| 2 | D3C/G157S/G250R/G283C | S101A |
| 3 | D3C/G157S/G250R/G283C | S101V |
| 4 | D3C/G157S/G250R/G283C | S101I |
| 5 | D3C/G157S/G250R/G283C | S101P |
| 6 | D3C/G157S/G250R/G283C | S101F |
| 7 | D3C/G157S/G250R/G283C | S101N |
| 8 | D3C/G157S/G250R/G283C | S101Q |
| 9 | D3C/G157S/G250R/G283C | S101Y |
| 10 | D3C/G157S/G250R/G283C | S101K |
| 11 | D3C/G157S/G250R/G283C | S101R |
| 12 | D3C/G157S/G250R/G283C | S101E |
| 13 | D3C/S101P/G250R/G283C | G157A |
| 14 | D3C/S101P/G250R/G283C | G157V |
| 15 | D3C/S101P/G250R/G283C | G157I |
| 16 | D3C/S101P/G250R/G283C | G157S |
| 17 | D3C/S101P/G250R/G283C | G157N |
| 18 | D3C/S101P/G250R/G283C | G157K |
| 19 | D3C/S101P/G250R/G283C | G157R |
| 20 | D3C/S101P/G250R/G283C | G157H |
| 21 | D3C/S101P/G250R/G283C | G157D |
| 22 | D3C/S101P/G250R/G283C | G157E |
| 23 | D3C/S101P/G157S/G283C | G250A |
| 24 | D3C/S101P/G157S/G283C | G250V |
| 25 | D3C/S101P/G157S/G283C | G250L |
| 26 | D3C/S101P/G157S/G283C | G250M |
| 27 | D3C/S101P/G157S/G283C | G250P |
| 28 | D3C/S101P/G157S/G283C | G250F |
| 29 | D3C/S101P/G157S/G283C | G250W |
| 30 | D3C/S101P/G157S/G283C | G250S |
| 31 | D3C/S101P/G157S/G283C | G250T |
| 32 | D3C/S101P/G157S/G283C | G250N |
| 33 | D3C/S101P/G157S/G283C | G250Q |
| 34 | D3C/S101P/G157S/G283C | G250Y |
| 35 | D3C/S101P/G157S/G283C | G250K |
| 36 | D3C/S101P/G157S/G283C | G250R |
| 37 | D3C/S101P/G157S/G283C | G250H |
| 38 | D3C/S101P/G157S/G283C | G250D |

Example 12

Crude Purification of Mutants that Underwent Amino Acid Substitutions and Evaluation of their Heat Resistance 3 ml of a CM2G medium supplemented with 25 μg/ml kanamycin was dispensed to each test tube. Each of the mutants generated in Example 11 was inoculated and precultured at 30° C. for 24 hours. 4 ml of an MM medium supplemented with 25 μg/ml kanamycin and 50 g/L $CaCO_3$ was dispensed to each test tube, and 0.2 ml of the preculture broth was subcultured. After cultivation at 30° C. for 5 hours, DTT was added to reach a concentration of 3 mM. After the addition of the DTT, each mutant was cultured at 30° C. for 43 hours. The culture broth was centrifuged (8,000 rpm, 10 minutes). The culture supernatant obtained was prepared to reach an enzyme concentration of 0.1 to 0.2 mg/mL, after which it was applied to the PD-10 column (manufactured by GE Healthcare) and exchanged with 20 mM sodium acetate buffer solution, pH 5.0, at room temperature to crudely purify the enzyme. Sodium hydroxide was carefully added to 3.0 mL of the crudely purified enzyme solution to reach a pH of 6.8 to 7.0; subtilisin in an amount 1/100 that of MTG was added, and a reaction was allowed to proceed at 30° C. for 16 hours to activate the mutated enzyme. The activated mutated enzyme solution was diluted 2 fold with 20 mM sodium phosphate buffer solution, pH 6.0. 100 µL of the 2-fold diluted enzyme solution was dispensed to a 96-well deep well; PMSF was added to reach 1 mM, and a reaction was allowed to proceed at 25° C. for 1 hour. The PMSF-treated enzyme solutions were heated at 25° C., 60° C., and 67° C., each for 10 minutes, using a thermal cycler. 20 µl of the heat-treated enzyme solution was dispensed to a 96-well well and warmed at 37° C. for 5 minutes in advance. 50 µL of liquid A (0.05 M MES, 0.1 M $NH_2OH$, 0.03 M CBZ-Gln-Gly, pH 6.0), previously warmed at 37° C. for 5 minutes, was dispensed to each well, and a reaction was allowed to proceed at 37° C. for 20 minutes, after which 50 µL of liquid B (1N HCl, 4% TCA, 1.67% $FeCl_3.6H_2O$) was dispensed to each well to stop the reaction, after which absorbance at 525 nm was measured using a plate reader. Taking the absorbance value of the 25° C.-heated enzyme solution as 100%, residual activities at 60° C. and 67° C. were calculated.

Figure 4A:
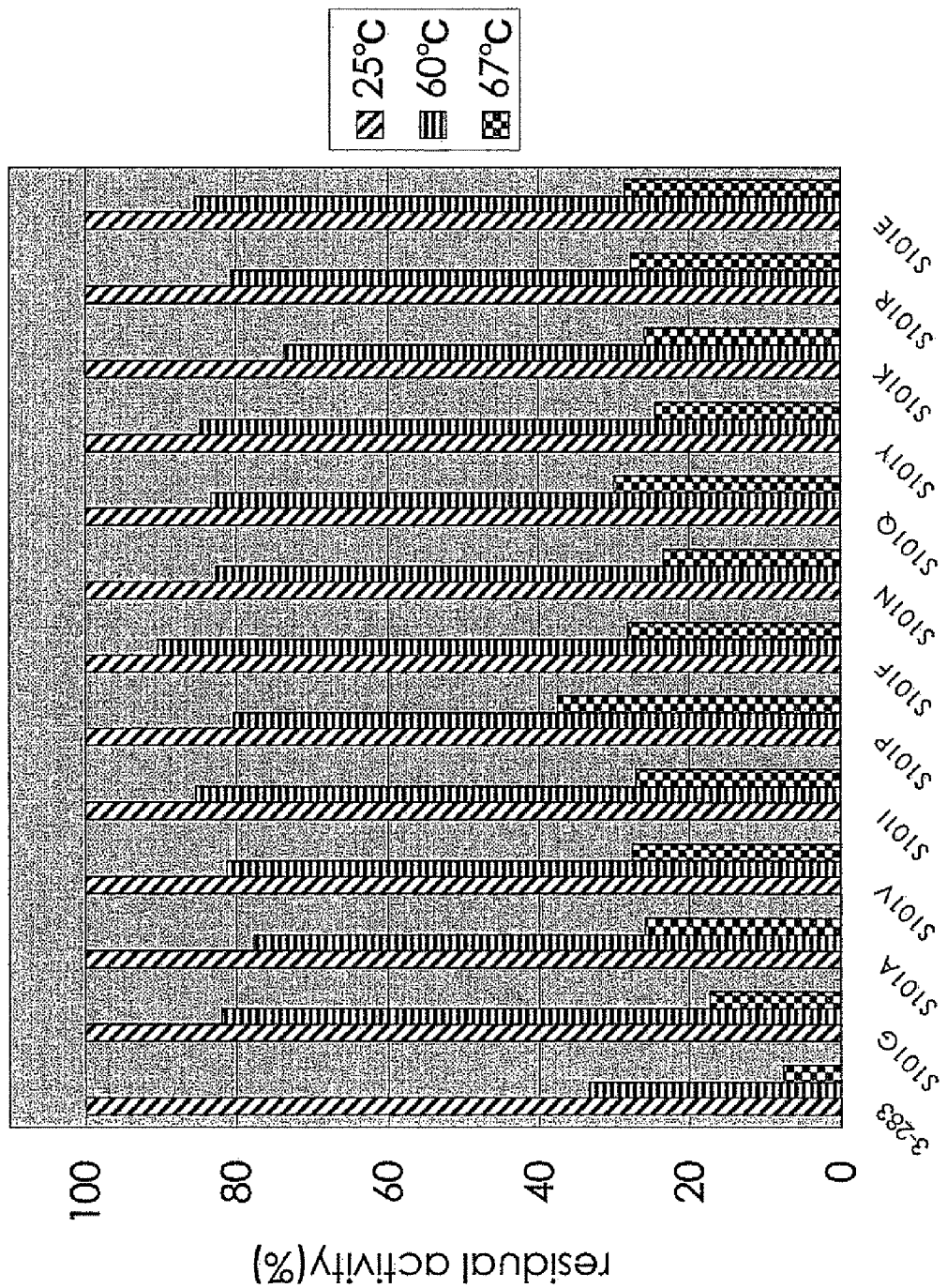
FIG. 4A is a graphic representation showing the results of an evaluation of the heat resistances of mutants listed in Table 6.
Figure 4B:
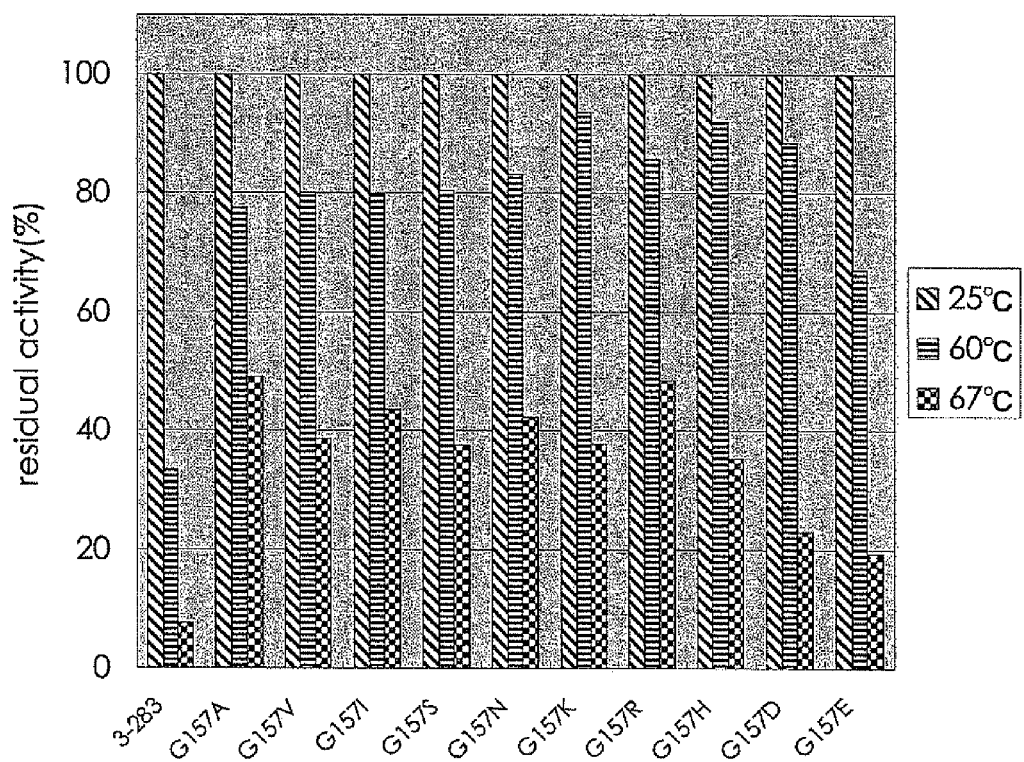
FIG. 4B is a graphic representation showing the results of an evaluation of the heat resistances of mutants listed in Table 6.

The results of the heat resistance evaluation are summarized in FIG. 4. In all of the mutants generated by introducing amino acid substitutions at S101 (G157→S and G250→R were also introduced as mutation points), the mutants generated by introducing amino acid substitutions at G157 (S101→P and G250→R were also introduced as mutation points), and the mutants generated by introducing amino acid substitutions at G250 (S101→P and G157→S were also introduced as mutation points), the residual activity after heat treatment at 67° C. for 10 minutes exceeded that of the control D3C/G283C (FIG. 4(A), (B), (C)). The results above demonstrated that the heat resistance of MTG was improved as amino acid substitutions were introduced at the three points of S101, G157, and G250.

Example 13

Introduction of Mutations into MSS2βB and Construction of Screening Library for the Mutants Obtained (Hereinafter Sometimes Referred to as MSS2βB Mutants)

The MTG gene consists of three regions: a pre-region, a pro-region, and a mature form a region. Mutations were introduced into the mature form region (about 1000 bp) that encodes the activity itself of MSS2βB (D3C/S101P/G157S/G250R/G283C) prepared by introducing the D3C and G283C mutations to form a disulfide bond (D3C/G283C), and further introducing the S101P, G157S, and G250R mutations to further improve the heat resistance, by error-prone PCR. Forward primer (TCCATAGCAATCCAAAGG (SEQ ID NO:13)) and Reverse primer (GGGCGAC-CGAGAAGTTTTTTACAAAAGGCA (SEQ ID NO:14)) were synthesized upstream and downstream, respectively, of the mature form region, and error-prone PCR was performed with the reaction liquid composition and conditions shown below, using the Genemorph Ver. 2 kit (manufactured by STRATAGENE), according to the procedure recommended by the manufacturer. The reaction liquid composition was set so that the mutations would be introduced into about three sites at the base sequence level. To ligate the PCR product obtained and the vector pPSPTG11, they were treated with BamHI (37° C., 2 hours), and then treated with Eco065I (37° C., 2 hours). The vector was cut out and dissolved in 60 µl of $ddH_2O$. The PCR product was purified by ethanol precipitation. After the vector and the PCR product were mixed together to make a ratio of 1:5, a reaction was allowed to proceed using Ligation Solution Kit I (manufactured by Takara Inc.) at 16° C. for 3 hours to ligate them. *E. coli* JM109 was transformed with the plasmid prepared by the ligation to yield 4500 colonies, which were subjected to plasmid extraction in sets of 500 colonies. YDK010 described in Example 1 was transformed with the extracted plasmid by electroporation. The transformant was cultured (30° C., 24 hours) on a CM2G plate (Glucose 5 g, Polypepton 10 g, Yeast extract 10 g, NaCl 5 g, DL-Met 0.2 g, pH 7.2/1 L) supplemented with 25 µg/ml kanamycin. The electroporation was performed by a method described in the literature (FEMS Microbiol. Lett., 53, 299-303, 1989).

Example 14

Primary Screening of MSS2βB Mutants 1 ml of a CM2G medium (Glucose 5 g, Polypepton 10 g, Yeast extract 10 g, NaCl 5 g, DL-Met 0.2 g, pH 7.2/1 L) supplemented with 25 µg/ml kanamycin was dispensed to each 96-well deep well. Each of the transformants (about 8200 strains) obtained in Example 13 was inoculated and precultured at 1,500 rpm, 30° C. for 24 hours. 1 ml of an MM medium (Glucose 60 g, $MgSO_4$ $7H_2O$ 1 g, $FeSO_4 7H_2O$ 0.01 g, $MnSO_4 5H_2O$ 0.01 g, $(NH_4)_2SO_4$ 30 g, $KH_2PO_4$ 1.5 g, VB1-HCl 0.45 mg, Biotin 0.45 mg, DL-Met 0.15 g, pH 7.5/1 L) supplemented with 25 µg/ml kanamycin and 50 g/L $CaCO_3$ was dispensed to each 96-well deep well, and 50 µl of the preculture broth was subcultured. After cultivation at 1,500 rpm, 30° C. for 5 hours, DTT was added to the 96-well deep well to reach a concentration of 3 mM. After the addition of the DTT, each transformant was cultured at 1500 rpm, 30° C. for 43 hours. The culture broth was centrifuged at 3000 rpm, 4° C. for 10 minutes, and 200 µL of the culture supernatant obtained was diluted 5 fold with 20 mM MOPS pH 7. Subtilisin in an amount 1/100 that of MTG was added to the dilution, and a reaction was allowed to proceed at 30° C. for 16 hours to activate the MTG. Screening was performed by measuring the activity by the hydroxamate method. In the measurement of the activity, 30 µl of the activated solution was dispensed to a 96-well well and warmed at 37° C. for 5 minutes in advance. 50 µL of liquid A (0.05 M MES, 0.1 M $NH_2OH$, 0.03 M CBZ-Gln-Gly, pH 6.0), previously warmed at 37° C. for 5 minutes, was dispensed to each well, and a reaction was allowed to proceed at 37° C. for 20 minutes, after which 50 µL of liquid B (1N HCl, 4% TCA, 1.67% $FeCl_36H_2O$) was dispensed to each well to stop the reaction, after which absorbance at 525 nm was measured using a plate reader. Next, 100 µL of the reaction liquid was dispensed to a 96-well deep well; PMSF was added to reach 1 mM, and a reaction was allowed to proceed at 25° C. for 1 hour. The PMSF-treated reaction liquid was heated at 67° C. for 10 minutes, using a thermal cycler. The heat-treated reaction liquid was subjected to the hydroxamate method to measure the activity as described above. With MSS2βB as the control, 171 strains whose absorbances before and after the heat treatment were nearly equivalent to those of the control and whose residual activities derived from the absorbances before and after the heat treatment were equivalent to or more than those of the control were selected.

Example 15

Mutation Point Analysis of Strains Selected by Primary Screening

Mutation points were analyzed by identifying the base sequences of the strains obtained by screening. Each strain obtained by the screening was cultured at 30° C. for 24 hours in a CM2G medium supplemented with 25 μg/ml kanamycin, after which the plasmid was extracted using the QIAprepSpin Miniprep Kit of QIAGEN, and the *E. coli* JM109 strain was transformed therewith. The transformed *E. coli* JM109 strain was cultured at 37° C. for 16 hours using LB medium, after which the plasmid was extracted in the same way. Base sequence analysis was performed using the ABI PRISM Cycle Sequencing Kit according to the procedure recommended by the manufacturer. As a result, 86 kinds of mutants were identified (Table 7).

TABLE 7

Table 7 Mutants identified by primary screening

| No. | | Amino acid substitution |
|---|---|---|
| 1 | 1-1-8B | S23P |
| 2 | 1-1-12B | Q39H/V326I |
| 3 | 1-2-2C | G122D |
| 4 | 1-2-12B | R97G/S144R/V311E |
| 5 | 1-3-6G | W59C |
| 6 | 1-3-9D | A267S |
| 7 | 1-3-10A | G47V/T321S |
| 8 | 1-4-4D | R21H |
| 9 | 2-1-12G | P323L |
| 10 | 2-3-5F | V65L |
| 11 | 2-3-12C | P9S |
| 12 | 2-4-11A | R208L |
| 13 | 2-4-11G | H188N |
| 14 | 2-4-12F | E54D |
| 15 | 2-5-6B | E54D |
| 16 | 2-7-10E | T53S/E119K |
| 17 | 2-7-12A | E55G/E119K/N163K/Y217H |
| 18 | 2-7-12G | N563K |
| 19 | 2-6-12B | N78D/R79T |
| 20 | 3-3-2B | S23T |
| 21 | 3-3-7H | S23T/L147F |
| 22 | 3-3-9D | A27P/L137P/D237N/E249G |
| 23 | 3-3-10A | G73D/V132I/K214M/S293N |
| 24 | 3-4-9A | E300K/T313I |
| 25 | 3-6-10E | D266E |
| 26 | 3-6-12E | K152M |
| 27 | 3-8-3C | V30A/N92Y/R105Q/A155V/P220Q |
| 28 | 5-3-3D | A130S |
| 29 | 5-3-6D | Q74H |
| 30 | 5-4-12C | E292V |
| 31 | 5-5-9C | P169L/G230S |
| 32 | 5-5-11A | D268N |
| 33 | 5-5-11E | W258C |
| 34 | 5-5-12G | D199Y |
| 35 | 5-7-7D | A145V |
| 36 | 5-7-8C | K294R |
| 37 | 6-1-10H | N88T |
| 38 | 6-4-7G | P241Q |
| 39 | 6-5-7D | H140L |
| 40 | 6-6-10B | A81T |
| 41 | 6-7-3A | S131T |
| 42 | 6-7-4E | E128G |
| 43 | 7-1-7H | G228S |
| 44 | 7-2-8D | L137M |
| 45 | 7-3-4C | S168T/T321S |
| 46 | 7-6-12B | M234L |
| 47 | 8-5-9D | R45G/E300D |
| 48 | 8-8-6F | P247A |
| 49 | 9-2-8A | D207G |
| 50 | 9-2-12C | R105W/D118Y/R208Q/E249V/T270I/R307H/I313N |
| 51 | 9-3-8C | W37R/H274L |
| 52 | 9-3-9B | T77R |
| 53 | 9-5-8A | N156S |
| 54 | 9-7-2A | V132L |
| 55 | 9-8-9E | D18N/S243G |
| 56 | 9-8-12B | R48K/E55K |
| 57 | 10-3-10A | N78D/R79T |
| 58 | 10-4-6E | E115D |
| 59 | 10-4-6G | Y75F |
| 60 | 10-5-4E | L80V |
| 61 | 10-5-6F | D221E/N282K/M288I |
| 62 | 10-5-9E | D148E/G205C/A287V |
| 63 | 10-5-11G | E249D |
| 64 | 10-6-3F | M288L |
| 65 | 10-6-10A | Q124R |
| 66 | 10-7-9E | S43I/R45S/W59R |
| 67 | 10-8-9E | V41I/P76Q/G248A |
| 68 | 11-3-10B | R238M |
| 69 | 11-7-12H | D148H/E249G |
| 70 | 11-8-12G | Q51E/A265T |
| 71 | 12-1-8D | E28D/F170C/A267V |
| 72 | 12-2-9A | R208W |
| 73 | 12-2-12D | A83V |
| 74 | 12-3-5C | L80P |
| 75 | 12-3-8H | P175W/D268E |
| 76 | 12-4-2C | G228S |
| 77 | 12-5-11H | A145P/A280S |
| 78 | 12-6-7A | R791/F259S |
| 79 | 12-6-8B | A27P/W59R |
| 80 | 12-6-9F | E249K |
| 81 | 12-6-11G | A160S |
| 82 | 12-7-10F | R127L/K152E |
| 83 | 12-8-3B | P8L/P178A/S210G |
| 84 | 12-8-6G | G73W/H188Y/270/D221V/T229S |
| 85 | 13-2-12B | T245S |
| 86 | 13-4-10A | A265T/M288I |

Example 16

Secondary Screening of MSS2βB Mutants 1 ml of a CM2G medium (Glucose 5 g, Polypepton 10 g, Yeast extract 10 g, NaCl 5 g, DL-Met 0.2 g, pH 7.2/1 L) supplemented with 25 μg/ml kanamycin was dispensed to each 96-well deep well. Of the 86 kinds of transformants selected in Example 15, 73 kinds incorporating a single mutation or a double mutation were inoculated in octuplicate and precultured at 1,500 rpm, 30° C. for 24 hours. 1 ml of an MM medium (Glucose 60 g, MgSO$_4$ 7H$_2$O 1 g, FeSO$_4$ 7H$_2$O 0.01 g, MnSO$_4$ 5H$_2$O 0.01 g, (NH$_4$)$_2$SO$_4$ 30 g, KH$_2$PO$_4$ 1.5 g, VB1-HCl 0.45 mg, Biotin 0.45 mg, DL-Met 0.15 g, pH 7.5/1 L) supplemented with 25 μg/ml kanamycin and 50 g/L CaCO$_3$ was dispensed to each 96-well deep well, and 50 μl of the preculture broth was subcultured. After cultivation at 1,500 rpm, 30° C. for 5 hours, DTT was added to the 96-well deep well to reach a concentration of 3 mM. After the addition of the DTT, each transformant was cultured at 1500 rpm, 30° C. for 43 hours. The culture broth was centrifuged at 3000 rpm, 4° C. for 10 minutes, and 200 μL of the culture supernatant obtained was diluted 5 fold with 20 mM MOPS pH 7. Subtilisin in an amount 1/100 that of MTG was added to the dilution, and a reaction was allowed to proceed at 30° C. for 16 hours to activate the MTG. Screening was performed by measuring the activity by the hydroxamate method. In the measurement of the activity, 30 μl of the activated solution was dispensed to each 96-well well and warmed at 37° C. for 5 minutes in advance. 50 μL of liquid A (0.05 M MES, 0.1 M NH$_2$OH, 0.03 M CBZ-Gln-Gly, pH 6.0), previously warmed at 37° C. for 5 minutes, was dispensed to each well; a reaction was allowed to proceed at 37° C. for 20 minutes, after which 50 μL of liquid B (1N HCl, 4% TCA, 1.67% FeCl$_3$ 6H$_2$O) was dispensed to each well to stop the reaction, after which absorbance at 525 nm was measured using a plate reader. Next, 100 μL of the reaction liquid was dispensed to each 96-well deep well; PMSF was added to reach 1 mM, and a reaction was allowed to proceed at 25° C. for 1 hour. The PMSF-treated reaction liquid was heated at 67° C. for 10 minutes, using a thermal cycler. The heat-treated reaction liquid was subjected to the hydroxamate method to measure the activity as described above. As a result of a measurement of the hydroxamate activity after heat treatment, 8 kinds of mutants (Table 8) exhibited a residual activity equivalent to, or more than, that of the control MSS2βB.

TABLE 8

Table 8 Mutants selected by secondary screening

|  | Amino acid substitution |
|---|---|
| 2-4-11A | R208L |
| 5-5-11A | D268N |
| 9-7-2A | V132L |
| 9-8-9E | D18N/S243G |
| 11-3-10B | R238M |
| 12-2-9A | R208W |
| 12-6-9F | E249K |
| 12-7-10F | R127L/K152E |

Example 17

Purification of MSS2βB Mutants Selected by Secondary Screening 3 ml of a CM2G medium supplemented with 25 μg/ml kanamycin was dispensed to each test tube. Each of the 8 kinds of mutants selected by secondary screening and the control (MSS2βB) was inoculated and precultured at 30° C. for 24 hours. An MM medium supplemented with 25 μg/ml kanamycin and 50 g/L CaCO$_3$ was dispensed to Sakaguchi flasks at 50 ml per flask, and 2.5 ml of the pre-culture broth was subcultured and cultivated at 30° C. for 48 hours. Subculture was performed. After cultivation at 30° C. for 5 hours, DTT was added to reach a concentration of 3 mM. After the addition of the DTT, each mutant was cultured at 30° C. for 43 hours. The culture broth was centrifuged (8,000 rpm, 10 minutes); subtilisin in an amount 1/100 that of MTG was added to the culture supernatant obtained, and a reaction was allowed to proceed at 30° C. for 16 hours to activate the MTG. The activated solution was exchanged with an equilibration buffer solution for cation exchange chromatography (20 mM sodium acetate buffer solution, pH 5.5) using Sephadex G25 (M). Next, the entire amount was applied to a cation exchange column (Resource S 6 ml; manufactured by GE Healthcare Bioscience) fully equilibrated with the same buffer solution. After re-equilibration with the same buffer solution, a protein fraction eluted at an NaCl concentration of nearly 200 mM on a linear concentration gradient of 0→0.5 M NaCl was fractionated with UV absorption at a wavelength of 280 nm as an index. The activities and protein contents of the fractions were measured by the above-described methods, and fractions near the peak top with nearly equivalent specific activity, excluding fractions of low specific activity, were recovered. The fractions recovered were passed through Sephadex G25(M) to replace the solvent with 20 mM phosphate buffer solution, pH 6.0. In all cases, chromatography was performed at room temperature.

Example 18

Evaluation of Heat Resistances of Purified Mutated Enzymes 8 kinds of purified mutated enzymes were prepared to reach 0.1 mg/mL. 100 μL of each enzyme solution was dispensed to a 96-well deep well; PMSF was added to reach 1 mM, and a reaction was allowed to proceed at 25° C. for 1 hour. The enzyme solutions were heated at 25° C., 67° C., and 70° C., each for 10 minutes, using a thermal cycler. 20 μl of the enzyme solution heat-treated above was dispensed to a 96-well well and warmed at 37° C. for 5 minutes in advance. 50 μl of liquid A (0.05 M MES, 0.1 M NH$_2$OH, 0.03 M CBZ-Gln-Gly, pH 6.0), previously warmed at 37° C. for 5 minutes, was dispensed to each well; a reaction was allowed to proceed at 37° C. for 20 minutes, after which 50 μl of liquid B (1N HCl, 4% TCA, 1.67% FeCl$_3$ 6H$_2$O) was dispensed to each well to stop the reaction, after which absorbance at 525 nm was measured using a plate reader. Taking the absorbance value of the 25° C.-heated enzyme solution as 100%, residual activities at 67° C. and 70° C. were calculated.

The results of the heat resistance evaluation are summarized in Table 9. It was found that the heat resistance was improved in 2-4-11A(R208L), 5-5-11A(D268N), 9-7-2A (V132L), 11-3-10B(R238M), 12-2-9A(R208W), and 12-6-9F(E249K) under the 70° C. conditions. Thereof, 2-4-11A (R208L) exhibited the highest residual activity. Because 12-2-9A (R208W) was extracted by screening, it was suggested that the heat resistance of MSS2βB was improved by the introduction of a mutation at R208.

TABLE 9

Table 9 Evaluation of heat resistances of purified mutated enzymes

| ID | mutaion point | residual Activ(67° C.) % | residual Activ.(70° C.) % |
|---|---|---|---|
| MSS2βB | — | 43.9 | 2.4 |
| 2-4-11A | R208L | 53.0 | 12.3 |
| 5-5-11A | D268N | 49.8 | 5.5 |
| 9-7-2A | V132L | 35.3 | 7.5 |
| 9-8-9E | D18N/S243G | 41.5 | 2.5 |
| 11-3-10B | R238M | 42.8 | 5.0 |
| 12-2-9A | R208W | 47.0 | 3.4 |
| 12-6-9F | E249K | 31.5 | 4.3 |
| 12-7-10F | R127L/K152E | 3.8 | 2.5 |

Example 19

Confirmation of Improved Heat Resistance of R208

The results in Example 18 showed that 2-4-11A(R208L) had improved heat resistance compared with MSS2βB. To confirm that the site of the mutation point R208→L introduced into MSS2βB contributes to an improvement of the heat resistance, verification by amino acid substitutions was performed. Specifically, mutants were constructed by introducing the amino acid substitution R208→A, L, I, W, N, Y or E into MSS2βB. Mutations for achieving the amino acid substitutions were introduced into MSS2βB, using the QuikChange II Site-Directed Mutagenesis Kit of Stratagene, as in Example 13. Introduction of the mutations was checked by analyzing the base sequence in the same manner as the above-described method. The constructed mutants are listed in Table 10. Each constructed plasmid was introduced into *Corynebacterium* by electroporation to yield transformants.

TABLE 10

Table 10 Combinations of promising mutation points

| No. | Mutation points introduced into natural-type MTG | Amino acid substitution |
|---|---|---|
| 1 | D3C/S101P/G157S/G250R/G283C | R208A |
| 2 | D3C/S101P/G157S/G250R/G283C | R208L |
| 3 | D3C/S101P/G157S/G250R/G283C | R208I |
| 4 | D3C/S101P/G157S/G250R/G283C | R208W |
| 5 | D3C/S101P/P157S/G250R/G283C | R208Y |
| 6 | D3C/S101P/G157S/G250R/G283C | R208N |
| 7 | D3C/S101P/G157S/G250R/G283C | R208E |

Example 20

Crude Purification of Mutants that Underwent Amino Acid Substitutions and Evaluation of Heat Resistance Thereof 3 ml of a CM2G medium supplemented with 25 µg/ml kanamycin was dispensed to each test tube. Each of the mutants generated in Example 19 was inoculated and precultured at 30° C. for 24 hours. 4 ml of an MM medium supplemented with 25 µg/ml kanamycin and 50 g/L CaCO$_3$ was dispensed to test tubes, and 0.2 ml of the preculture broth was subcultured. After cultivation at 30° C. for 5 hours, DTT was added to reach a concentration of 3 mM. After the addition of the DTT, the mutant was cultured at 30° C. for 43 hours. The culture broth was centrifuged (8,000 rpm, 10 minutes). The culture supernatant obtained was prepared to reach an enzyme concentration of 0.1 to 0.2 mg/mL, after which it was applied to the PD-10 column (manufactured by GE Healthcare) and exchanged with 20 mM sodium acetate buffer solution, pH 5.0, at room temperature to crudely purify the enzyme. Sodium hydroxide was carefully added to 3.0 mL of the crudely purified enzyme solution to reach a pH of 6.8 to 7.0; subtilisin in an amount 1/100 that of MTG was added, and a reaction was allowed to proceed at 30° C. for 16 hours to activate the mutated enzyme. The activated mutated enzyme solution was diluted 2 fold with 20 mM sodium phosphate buffer solution, pH 6.0. 100 µL of the 2-fold diluted enzyme solution was dispensed to a 96-well deep well; PMSF was added to reach 1 mM, and a reaction was allowed to proceed at 25° C. for 1 hour. The PMSF-treated enzyme solutions were heated at 25° C., 60° C., and 67° C., each for 10 minutes, using a thermal cycler. 20 µl of the enzyme solution heat-treated above was dispensed to a 96-well well and warmed at 37° C. for 5 minutes in advance. 50 µL of liquid A (0.05 M MES, 0.1 M NH$_2$OH, 0.03 M CBZ-Gln-Gly, pH 6.0), previously warmed at 37° C. for 5 minutes, was dispensed to each well, and a reaction was allowed to proceed at 37° C. for 20 minutes, after which 50 µL of liquid B (1N HCl, 4% TCA, 1.67% FeCl$_3$ 6H$_2$O) was dispensed to each well to stop the reaction, after which absorbance at 525 nm was measured using a plate reader. Taking the absorbance value of the 25° C.-heated enzyme solution as 100%, residual activities at 60° C. and 67° C. were calculated.

Figure 5:
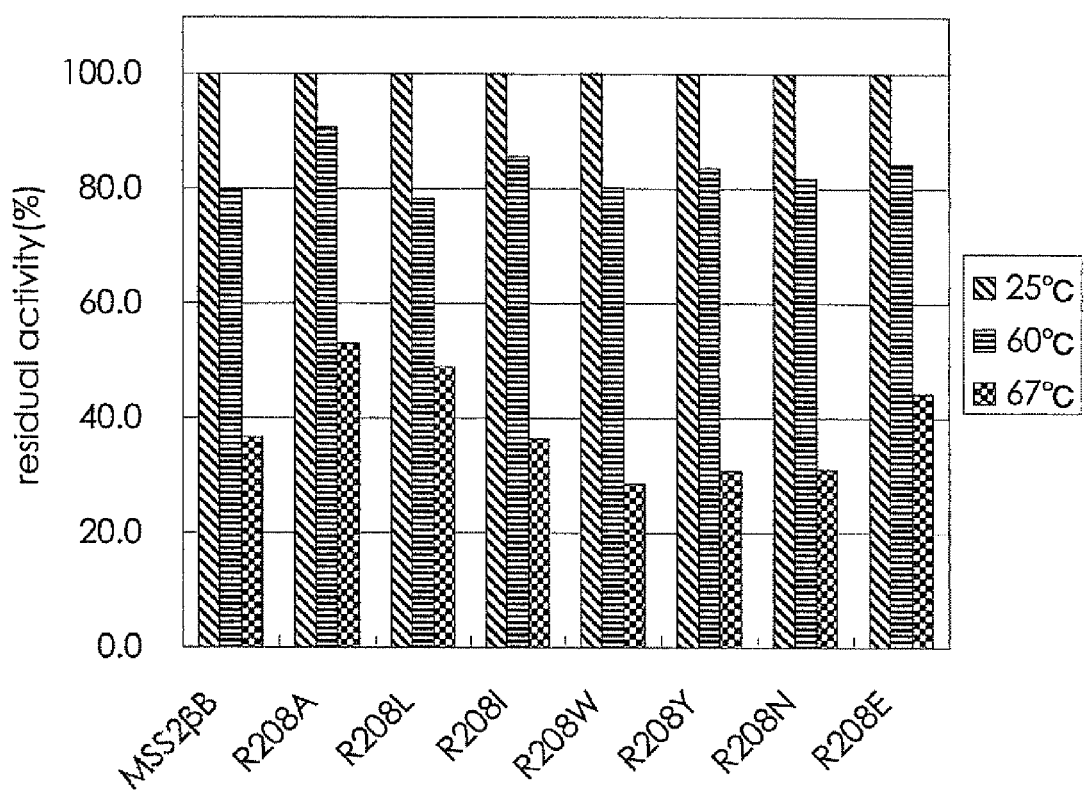
FIG. 5 is a drawing showing the results of the heat resistance evaluation in various mutants generated by amino acid substitutions at R208 of MSS2βB.

The results of the heat resistance evaluation are summarized in FIG. 5. Regarding the mutants generated by amino acid substitutions at R208 of MSS2βB, in the case of the three amino acid substitutions R208A, R208L, and R208E, the residual activities after heat treatment at 67° C. for 10 minutes exceeded that of the control MSS2βB. The results above demonstrated that the heat resistance of MSS2βB improved when R208 was substituted with A or L or E.

Example 21

Combinations of Promising Mutation Points

From the results of Example 18, it was found that the heat resistance improved when 2-4-11A (R208L) was introduced into MSS2βB. Hence, each of the other mutation points extracted in Example 18, that is, V132L, R238M, E249K, and D268N, was introduced into 2-4-11A(R208L) to generate multiple mutants, and the heat resistance improving effects were checked. The mutations were introduced into 2-4-11A (R208L), using the QuikChange II Site-Directed Mutagenesis Kit of Stratagene, as in Example 13. Introduction of the mutations was checked by analyzing the base sequence in the same manner as the above. The constructed mutants are listed in Table 11.

TABLE 11

Table 11 Combinations of promising mutation points

| No. | Mutation points introduced into natural-type MTG | Amino acid substitution |
|---|---|---|
| 1 | D3C/S101P/G157S/R208L/G250R/G283C | V132L |
| 2 | D3C/S101P/G157S/R208L/G250R/G283C | R238M |
| 3 | D3C/S101P/G157S/R208L/G250R/G283C | E249K |
| 4 | D3C/S101P/G157S/R208L/G250R/G283C | D268N |

Example 22

Evaluation of Heat Resistances of Promising Multiple Mutants

Each of the plasmids constructed in Example 21 was introduced into *Corynebacterium* by electroporation to yield transformants. 3 ml of a CM2G medium supplemented with 25 µg/ml kanamycin was dispensed to each test tube. Each transformant obtained was inoculated and precultured at 30° C. for 24 hours. 4 ml of an MM medium supplemented with 25 µg/ml kanamycin and 50 g/L CaCO$_3$ was dispensed to each test tube, and 0.2 ml of the preculture broth was subcultured. After cultivation at 30° C. for 5 hours, DTT was added to reach a concentration of 3 mM. After the addition of the DTT, the transformant was cultured at 30° C. for 43 hours. The culture broth was centrifuged (8,000 rpm, 10 minutes). The culture supernatant obtained was prepared to reach an enzyme concentration of 0.1 to 0.2 mg/mL, after which it was applied to the PD-10 column (manufactured by GE Healthcare) and exchanged with 20 mM sodium acetate buffer solution, pH 5.0, at room temperature to crudely purify the enzyme. Sodium hydroxide was carefully added to 3.0 mL of the crudely purified enzyme solution to reach a pH of 6.8 to 7.0; subtilisin in an amount 1/100 that of MTG was added, and a reaction was allowed to proceed at 30° C. for 16 hours to activate the mutated enzyme. The activated mutated enzyme solution was diluted 2 fold with 20 mM sodium phosphate buffer solution, pH 6.0. 100 µL of the 2-fold diluted enzyme solution was dispensed to a 96-well deep well; PMSF was added to reach 1 mM, and a reaction was allowed to proceed at 25° C. for 1 hour. The PMSF-treated enzyme solutions were heated at 25° C., 60° C., and 67° C., each for 10 minutes, using a thermal cycler. 20 μl of the enzyme solution heat-treated above was dispensed to a 96-well well and warmed at 37° C. for 5 minutes in advance. 50 μL of liquid A (0.05 M MES, 0.1 M NH$_2$OH, 0.03 M CBZ-Gln-Gly, pH 6.0), previously warmed at 37° C. for 5 minutes, was dispensed to each well, and a reaction was allowed to proceed at 37° C. for 20 minutes, after which 50 μL of liquid B (1N HCl, 4% TCA, 1.67% FeCl$_3$.6H$_2$O) was dispensed to each well to stop the reaction, after which absorbance at 525 nm was measured using a plate reader. Taking the absorbance value of the 25° C.-heated enzyme solution as 100%, residual activities at 60° C. and 67° C. were calculated.

Figure 6:
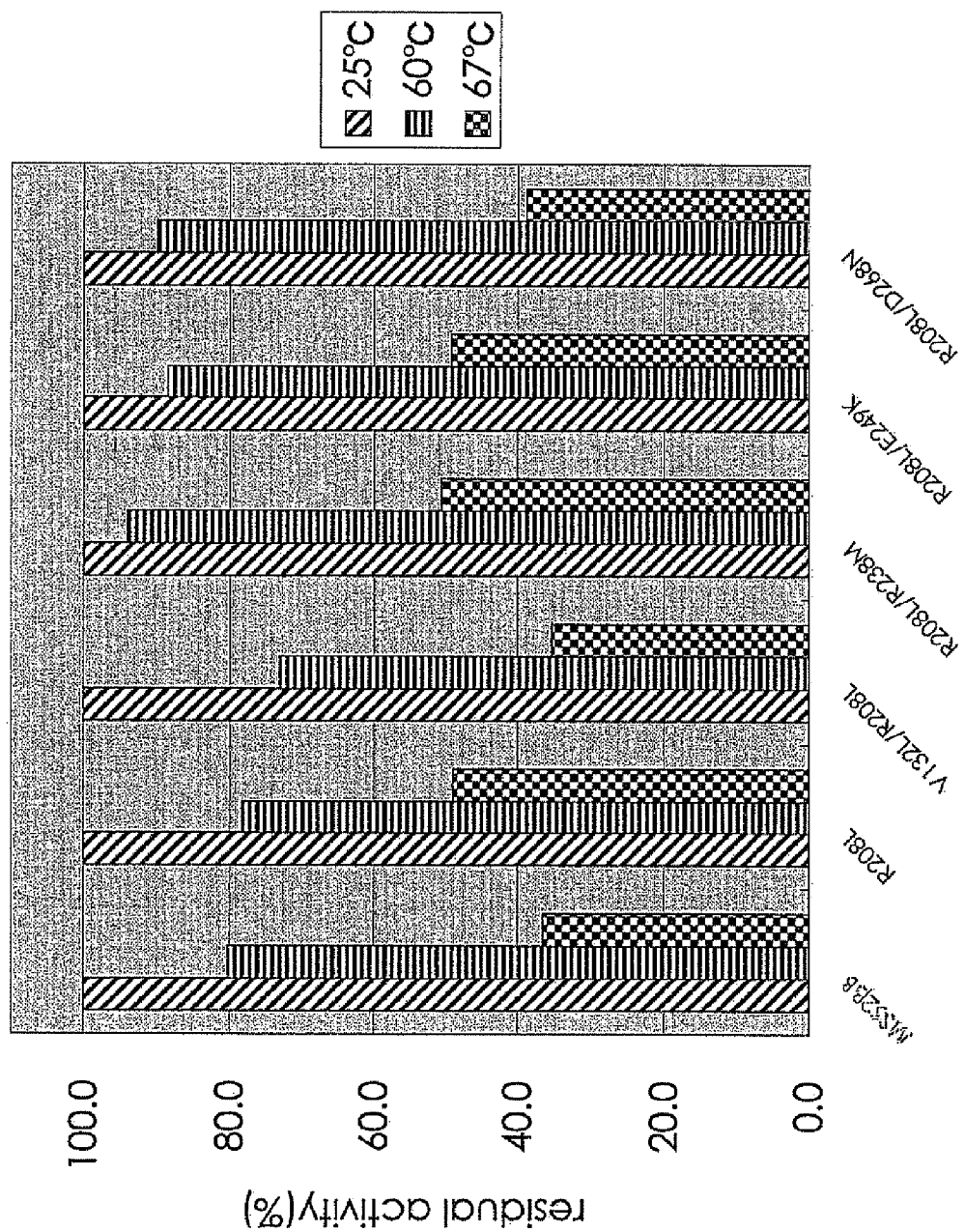
FIG. 6 is a graphic representation showing the results of an evaluation of the heat resistances in mutants listed in Table 11.

The results of the heat resistance evaluation are summarized in FIG. 6. Even when each of V132L, R238M, E249K, and D268N was introduced into 2-4-11A(R208L), the heat resistance was not improved.

Example 23

Evaluation of pH Stability of MSS2βB 0.5 to 0.6 mg/ml of each of MTG, the D3C/G283C(3-283) mutant and MSS2βB was diluted 4 fold with a given buffer solution (0.1 M glycine buffer solution pH 3, 0.1 M sodium phosphate buffer solution pH 12); this dilution was allowed to stand at room temperature for 1 hour then diluted 2 fold with 0.4 M phosphate buffer solution pH 6, and the activity was measured by the hydroxamate method. The results are shown in Table 12 with activity at pH 6 as 100%. MSS2βB was found to have slightly improved levels of acid resistance at pH 3 and alkali resistance at pH 12 compared with D3C/G283C.

TABLE 12

| Table 12 Evaluation of pH stability | | | |
|---|---|---|---|
| | pH 3.0 | pH 6.0 | pH 12.0 |
| MTG | 28.7 | 100.0 | 7.3 |
| D3C-G283C | 91.4 | 100.0 | 39.4 |
| MSS2βB | 95.2 | 100.0 | 39.9 |

INDUSTRIAL APPLICABILITY

According to the present invention, it is possible to provide transglutaminases with improved heat resistance by modifying MTGs. Furthermore, novel products and novel techniques can be provided by using transglutaminases with improved heat resistance.

This application is based on patent application No. 2009-053537 filed in Japan, and the contents disclosed therein are hereby entirely incorporated by reference. In addition, the patent documents and non-patent documents cited in the present specification are hereby incorporated in their entireties by reference, to the extent that they have been disclosed in the present specification.

The invention claimed is:

1. An isolated protein having transglutaminase activity, and comprising an amino acid sequence selected from the group consisting of:
   (A) the amino acid sequence of SEQ ID NO: 2, but having a mutation to cysteine at the 3-position and 283-position, and also having a mutation at a position selected from the group consisting of the 101-position, 157-position, 250-position, and combinations thereof;
   (B) the amino acid sequence selected from the group consisting of SEQ ID NO: 4, 6, 8, and 12, but having a mutation to cysteine at positions corresponding to positions in SEQ ID NO: 2 of the 3-position and 283-position, and also having a mutation at a position corresponding to a position in SEQ ID NO:2 selected from the group consisting of the 101-position, 157-position, 250-position, and combinations thereof; and
   (C) an amino acid sequence which is at least 95% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof.

2. An isolated protein having transglutaminase activity, and comprising the amino acid sequence selected from the group consisting of:
   (A) the amino acid sequence of SEQ ID NO: 2, but having a mutation to cysteine at the 2-position and 282-position, and also having a mutation at a position selected from the group consisting of the 101-position, 157-position, 250-position, and combinations thereof;
   (B) the amino acid sequence selected from the group consisting of SEQ ID NO: 4, 6, 8, and 12, but having a mutation to cysteine at positions corresponding to positions in SEQ ID NO: 2 of the 2-position and 282-position, and also having a mutation of a position corresponding to a position in SEQ ID NO: 2 selected from the group consisting of the 101-position, 157-position, 250-position, and combinations thereof; and
   (C) an amino acid sequence which is at least 95% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof.

3. An isolated protein having transglutaminase activity, and comprising the amino acid sequence selected from the group consisting of:
   (A) the amino acid sequence of SEQ ID NO: 2, but having a mutation to cysteine at the 2-position and 283-position, and also having a mutation at a position selected from the group consisting of the 101-position, 157-position, 250-position, and combinations thereof;
   (B) the amino acid sequence selected from the group consisting of SEQ ID NO: 4, 6, 8, 10, and 12, but having a mutation to cysteine at positions corresponding to positions in SEQ ID NO: 2 of the 2-position and 283-position, and also having a mutation at a position corresponding to a position in SEQ ID NO: 2 selected from the group consisting of the 101-position, 157-position, 250-position, and combinations thereof; and
   (C) an amino acid sequence which is at least 95% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof.

4. An isolated protein having transglutaminase activity, and comprising an amino acid sequence selected from the group consisting of:
   (A) the amino acid sequence of SEQ ID NO: 2, but having a mutation to cysteine at the 7-position and 58-position, and also having a mutation at a position selected from the group consisting of the 101-position, 157-position, 250-position, and combinations thereof;
   (B) the amino acid sequence selected from the group consisting of SEQ ID NO: 4, 6, 8, 10, and 12, but having a mutation to cysteine at positions corresponding to positions in SEQ ID NO: 2 of the 7-position and 58-position, and also having a mutation at a position corresponding to a position in SEQ ID NO: 2 selected from the group consisting of the 101-position, 157-position, 250-position, and combinations thereof; and
   (C) an amino acid sequence which is at least 95% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof.

5. The protein according to claim 1, wherein the mutation at the 101-position is a mutation to proline, the mutation at the 157-position is a mutation to alanine or serine, the mutation at the 250-position is a mutation to alanine or arginine.

6. The protein according to claim 1, wherein the protein has a mutation of the aspartic acid at the 3-position to cysteine, a mutation of the serine at the 101-position to proline, a mutation of the glycine at the 157-position to serine, a mutation of glycine at the 250-position to arginine, and a mutation of the glycine at the 283-position to cysteine.

7. The protein according to claim 1, wherein the protein further has a set of mutations selected from the group consisting of:
   (1) mutation of 101-position from serine to proline, mutation of 157-position from glycine to serine, and mutation of 250-position from glycine to an amino acid selected from the group consisting of alanine, valine, leucine, methionine, proline, phenylalanine, tryptophan, serine, threonine, asparagine, glutamine, tyrosine, lysine, arginine, histidine, and aspartic acid;
   (2) mutation of 157-position from glycine to serine, mutation of 250-position from glycine to arginine, and mutation of 101-position from serine to an amino acid selected from the group consisting of glycine, alanine, valine, isoleucine, proline, phenylalanine, asparagine, glutamine, tyrosine, lysine, arginine, and glutamic acid; and
   (3) mutation of 101-position from serine to proline, mutation of 250-position from glycine to arginine, and mutation of 157-position from glycine to an amino acid selected from the group consisting of alanine, valine, isoleucine, serine, asparagine, lysine, arginine, histidine, aspartic acid and glutamic acid.

8. The protein according to claim 1, wherein the protein further has mutation of 101-position from serine to proline; mutation of 157-position from glycine to alanine, serine or arginine; and mutation of 250-position from glycine to alanine, phenylalanine, serine, asparagine or arginine.

9. The protein according to claim 8, wherein the protein further has a set of mutations selected from the group consisting of:
   (1) mutation of 101-position from serine to proline, mutation of 157-position from glycine to serine, and mutation of 250-position from glycine to alanine, phenylalanine, serine, asparagine or arginine;
   (2) mutation of 157-position from glycine to serine, mutation of 250-position from glycine to arginine, and mutation of 101-position from serine to proline; and
   (3) mutation of 101-position from serine to proline, mutation of 250-position from glycine to arginine, and mutation of 157-position from glycine to alanine, serine or arginine.

10. The protein according to claim 5, wherein the protein further comprises mutation of the 208-position from arginine to leucine, alanine, or glutamic acid.

11. The protein according to claim 6, wherein the protein further comprises:
    (1) mutation of 208-position from arginine to tryptophan,
    (2) mutation of 268-position from aspartic acid to asparagine,
    (3) mutation of 132-position from valine to leucine,
    (4) mutation of 238-position from arginine to methionine, or
    (5) mutation of 249-position from glutamic acid to lysine.

12. A method of processing a substrate protein, comprising the step of allowing a protein produced by the method according to claim 1 to act on a substrate protein.

13. The method according to claim 12, wherein the processing of a substrate protein is performed at 40° C. to 100° C.

14. A method of processing a substrate protein, comprising the step of allowing a protein produced by the method according to claim 1 to act on a substrate protein.

15. A method of processing a substrate protein, comprising the step of allowing a protein produced by the method according to claim 2 to act on a substrate protein.

16. The method according to claim 14, wherein the processing of a substrate protein is performed at 40° C. to 100° C.

17. The method according to claim 15, wherein the processing of a substrate protein is performed at 40° C. to 100° C.

18. An isolated protein having transglutaminase activity, and comprising an amino acid sequence selected from the group consisting of:
   (A) an amino acid sequence which is at least 95% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof; and
   (B) an amino acid sequence which is at least 98% homologous to the amino acid sequence selected from the group consisting of SEQ ID NO: 2, 4, 6, 8, 10 and 12, but comprising a mutation at a position corresponding to a position in SEQ ID NO: 2 selected from the group consisting of the 101-position, 157-position, 250-position, and combinations thereof.

* * * * *

SEQUENCE LISTING

<160> NUMBER OF SEQ ID NOS: 14

<210> SEQ ID NO 1
<211> LENGTH: 993
<212> TYPE: DNA
<213> ORGANISM: Streptomyces mobaraensis
<220> FEATURE:
<221> NAME/KEY: CDS
<222> LOCATION: (1)..(993)

<400> SEQUENCE: 1

```
gac tcc gac gac agg gtc acc cct ccc gcc gag ccg ctc gac agg atg    48
Asp Ser Asp Asp Arg Val Thr Pro Pro Ala Glu Pro Leu Asp Arg Met
1               5                   10                  15 ccc gac ccg tac cgt ccc tcg tac ggc agg gcc gag acg gtc gtc aac    96
Pro Asp Pro Tyr Arg Pro Ser Tyr Gly Arg Ala Glu Thr Val Val Asn
            20                  25                  30 aac tac ata cgc aag tgg cag cag gtc tac agc cac cgc gac ggc agg   144
Asn Tyr Ile Arg Lys Trp Gln Gln Val Tyr Ser His Arg Asp Gly Arg
        35                  40                  45 aag cag cag atg acc gag gag cag cgg gag tgg ctg tcc tac ggc tgc   192
Lys Gln Gln Met Thr Glu Glu Gln Arg Glu Trp Leu Ser Tyr Gly Cys
    50                  55                  60 gtc ggt gtc acc tgg gtc aat tcg ggt cag tac ccg acg aac aga ctg   240
Val Gly Val Thr Trp Val Asn Ser Gly Gln Tyr Pro Thr Asn Arg Leu
65                  70                  75                  80 gcc ttc gcg tcc ttc gac gag gac agg ttc aag aac gag ctg aag aac   288
Ala Phe Ala Ser Phe Asp Glu Asp Arg Phe Lys Asn Glu Leu Lys Asn
                85                  90                  95 ggc agg ccc cgg tcc ggc gag acg cgg gcg gag ttc gag ggc cgc gtc   336
Gly Arg Pro Arg Ser Gly Glu Thr Arg Ala Glu Phe Glu Gly Arg Val
            100                 105                 110 gcg aag gag agc ttc gac gag gag aag ggc ttc cag cgg gcg cgt gag   384
```

```
Ala Lys Glu Ser Phe Asp Glu Glu Lys Gly Phe Gln Arg Ala Arg Glu
        115                 120                 125 gtg gcg tcc gtc atg aac agg gcc ctg gag aac gcc cac gac gag agc    432
Val Ala Ser Val Met Asn Arg Ala Leu Glu Asn Ala His Asp Glu Ser
130                 135                 140 gct tac ctc gac aac ctc aag aag gaa ctg gcg aac ggc aac gac gcc    480
Ala Tyr Leu Asp Asn Leu Lys Lys Glu Leu Ala Asn Gly Asn Asp Ala
145                 150                 155                 160 ctg cgc aac gag gac gcc cgt tcc ccg ttc tac tcg gcg ctg cgg aac    528
Leu Arg Asn Glu Asp Ala Arg Ser Pro Phe Tyr Ser Ala Leu Arg Asn
            165                 170                 175 acg ccg tcc ttc aag gag cgg aac gga ggc aat cac gac ccg tcc agg    576
Thr Pro Ser Phe Lys Glu Arg Asn Gly Gly Asn His Asp Pro Ser Arg
        180                 185                 190 atg aag gcc gtc atc tac tcg aag cac ttc tgg agc ggc cag gac cgg    624
Met Lys Ala Val Ile Tyr Ser Lys His Phe Trp Ser Gly Gln Asp Arg
    195                 200                 205 tcg agt tcg gcc gac aag agg aag tac ggc gac ccg gac gcc ttc cgc    672
Ser Ser Ser Ala Asp Lys Arg Lys Tyr Gly Asp Pro Asp Ala Phe Arg
210                 215                 220 ccc gcc ccg ggc acc ggc ctg gtc gac atg tcg agg gac agg aac att    720
Pro Ala Pro Gly Thr Gly Leu Val Asp Met Ser Arg Asp Arg Asn Ile
225                 230                 235                 240 ccg cgc agc ccc acc agc ccc ggt gag gga ttc gtc aat ttc gac tac    768
Pro Arg Ser Pro Thr Ser Pro Gly Glu Gly Phe Val Asn Phe Asp Tyr
            245                 250                 255 ggc tgg ttc ggc gcc cag acg gaa gcg gac gcc gac aag acc gtc tgg    816
Gly Trp Phe Gly Ala Gln Thr Glu Ala Asp Ala Asp Lys Thr Val Trp
        260                 265                 270 acc cac gga aat cac tat cac gcg ccc aat ggc agc ctg ggt gcc atg    864
Thr His Gly Asn His Tyr His Ala Pro Asn Gly Ser Leu Gly Ala Met
    275                 280                 285 cat gtc tac gag agc aag ttc cgc aac tgg tcc gag ggt tac tcg gac    912
His Val Tyr Glu Ser Lys Phe Arg Asn Trp Ser Glu Gly Tyr Ser Asp
290                 295                 300 ttc gac cgc gga gcc tat gtg atc acc ttc atc ccc aag agc tgg aac    960
Phe Asp Arg Gly Ala Tyr Val Ile Thr Phe Ile Pro Lys Ser Trp Asn
305                 310                 315                 320 acc gcc ccc gac aag gta aag cag ggc tgg ccg                        993
Thr Ala Pro Asp Lys Val Lys Gln Gly Trp Pro
            325                 330

<210> SEQ ID NO 2
<211> LENGTH: 331
<212> TYPE: PRT
<213> ORGANISM: Streptomyces mobaraensis

<400> SEQUENCE: 2

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95
```

```
Gly Arg Pro Arg Ser Gly Glu Thr Arg Ala Glu Phe Glu Gly Arg Val
                100                 105                 110

Ala Lys Glu Ser Phe Asp Glu Lys Gly Phe Gln Arg Ala Arg Glu
        115                 120                 125

Val Ala Ser Val Met Asn Arg Ala Leu Glu Asn Ala His Asp Glu Ser
130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 3
<211> LENGTH: 990
<212> TYPE: DNA
<213> ORGANISM: Streptomyces cinnamoneus
<220> FEATURE:
<221> NAME/KEY: CDS
<222> LOCATION: (1)..(990)

<400> SEQUENCE: 3 tcc gat gac cgg gaa act cct ccc gcc gag ccg ctc gac agg atg cct      48
Ser Asp Asp Arg Glu Thr Pro Pro Ala Glu Pro Leu Asp Arg Met Pro
1               5                   10                  15 gag gcg tac cgg gcc tac gga ggc agg gcc act acg gtc gtc aac aac      96
Glu Ala Tyr Arg Ala Tyr Gly Gly Arg Ala Thr Thr Val Val Asn Asn
            20                  25                  30 tac ata cgc aag tgg cag cag gtc tac agt cac cgc gac gga aag aaa     144
Tyr Ile Arg Lys Trp Gln Gln Val Tyr Ser His Arg Asp Gly Lys Lys
        35                  40                  45 cag caa atg acc gaa gag cag cga gaa aag ctg tcc tac ggt tgc gtt     192
Gln Gln Met Thr Glu Glu Gln Arg Glu Lys Leu Ser Tyr Gly Cys Val
    50                  55                  60 ggc gtc acc tgg gtc aac tcg ggc ccc tac ccg acg aac aga ttg gcg     240
Gly Val Thr Trp Val Asn Ser Gly Pro Tyr Pro Thr Asn Arg Leu Ala
65                  70                  75                  80 ttc gcg tcc ttc gac gag aac aag tac aag aac gac ctg aag aac acc     288
Phe Ala Ser Phe Asp Glu Asn Lys Tyr Lys Asn Asp Leu Lys Asn Thr
                85                  90                  95
```

```
agc ccc cga ccc gat gaa acg cgg gcg gag ttc gag ggt cgc atc gcc      336
Ser Pro Arg Pro Asp Glu Thr Arg Ala Glu Phe Glu Gly Arg Ile Ala
        100                 105                 110 aag ggc agt ttc gac gag ggg aag ggt ttc aag cgg gcg cgt gat gtg      384
Lys Gly Ser Phe Asp Glu Gly Lys Gly Phe Lys Arg Ala Arg Asp Val
            115                 120                 125 gcg tcc gtc atg aac aag gcc ctg gaa aat gcc cac gac gag ggg act      432
Ala Ser Val Met Asn Lys Ala Leu Glu Asn Ala His Asp Glu Gly Thr
130                 135                 140 tac atc aac aac ctc aag acg gag ctc acg aac aac aat gac gct ctg      480
Tyr Ile Asn Asn Leu Lys Thr Glu Leu Thr Asn Asn Asn Asp Ala Leu
145                 150                 155                 160 ctc cgc gag gac agc cgc tcg aac ttc tac tcg gcg ctg agg aac aca      528
Leu Arg Glu Asp Ser Arg Ser Asn Phe Tyr Ser Ala Leu Arg Asn Thr
                165                 170                 175 ccg tcc ttc aag gaa agg gac ggc ggc aac tac gac ccg tcc aag atg      576
Pro Ser Phe Lys Glu Arg Asp Gly Gly Asn Tyr Asp Pro Ser Lys Met
            180                 185                 190 aag gcg gtg atc tac tcg aag cac ttc tgg agc ggg cag gac cag cgg      624
Lys Ala Val Ile Tyr Ser Lys His Phe Trp Ser Gly Gln Asp Gln Arg
        195                 200                 205 ggc tcc tcc gac aag agg aag tac ggc gac ccg gaa gcc ttc cgc ccc      672
Gly Ser Ser Asp Lys Arg Lys Tyr Gly Asp Pro Glu Ala Phe Arg Pro
210                 215                 220 gac cag ggt acc ggc ctg gtc gac atg tcg aag gac aga agc att ccg      720
Asp Gln Gly Thr Gly Leu Val Asp Met Ser Lys Asp Arg Ser Ile Pro
225                 230                 235                 240 cgc agt ccg gcc aag ccc ggc gaa ggt tgg gtc aat ttc gac tac ggt      768
Arg Ser Pro Ala Lys Pro Gly Glu Gly Trp Val Asn Phe Asp Tyr Gly
                245                 250                 255 tgg ttc ggg gct caa aca gaa gcg gat gcc gac aaa acc aca tgg acc      816
Trp Phe Gly Ala Gln Thr Glu Ala Asp Ala Asp Lys Thr Thr Trp Thr
            260                 265                 270 cac ggc gac cac tac cac gcg ccc aat agc gac ctg ggc ccc atg cac      864
His Gly Asp His Tyr His Ala Pro Asn Ser Asp Leu Gly Pro Met His
        275                 280                 285 gta cac gag agc aag ttc cgg aag tgg tct gcc ggg tac gcg gac ttc      912
Val His Glu Ser Lys Phe Arg Lys Trp Ser Ala Gly Tyr Ala Asp Phe
290                 295                 300 gac cgc gga gcc tac gtg atc acg ttc ata ccc aag agc tgg aac acc      960
Asp Arg Gly Ala Tyr Val Ile Thr Phe Ile Pro Lys Ser Trp Asn Thr
305                 310                 315                 320 gcc ccc gcc aag gtg gag caa ggc tgg ccg                              990
Ala Pro Ala Lys Val Glu Gln Gly Trp Pro
                325                 330

<210> SEQ ID NO 4
<211> LENGTH: 330
<212> TYPE: PRT
<213> ORGANISM: Streptomyces cinnamoneus

<400> SEQUENCE: 4

Ser Asp Asp Arg Glu Thr Pro Pro Ala Glu Pro Leu Asp Arg Met Pro
1               5                   10                  15

Glu Ala Tyr Arg Ala Tyr Gly Gly Arg Ala Thr Thr Val Val Asn Asn
            20                  25                  30

Tyr Ile Arg Lys Trp Gln Gln Val Tyr Ser His Arg Asp Gly Lys Lys
        35                  40                  45

Gln Gln Met Thr Glu Glu Gln Arg Glu Lys Leu Ser Tyr Gly Cys Val
    50                  55                  60
```

```
Gly Val Thr Trp Val Asn Ser Gly Pro Tyr Pro Thr Asn Arg Leu Ala
 65                  70                  75                  80

Phe Ala Ser Phe Asp Glu Asn Lys Tyr Lys Asn Asp Leu Lys Asn Thr
                 85                  90                  95

Ser Pro Arg Pro Asp Glu Thr Arg Ala Glu Phe Glu Gly Arg Ile Ala
            100                 105                 110

Lys Gly Ser Phe Asp Glu Gly Lys Gly Phe Lys Arg Ala Arg Asp Val
        115                 120                 125

Ala Ser Val Met Asn Lys Ala Leu Glu Asn Ala His Asp Glu Gly Thr
130                 135                 140

Tyr Ile Asn Asn Leu Lys Thr Glu Leu Thr Asn Asn Asp Ala Leu
145                 150                 155                 160

Leu Arg Glu Asp Ser Arg Ser Asn Phe Tyr Ser Ala Leu Arg Asn Thr
                165                 170                 175

Pro Ser Phe Lys Glu Arg Asp Gly Gly Asn Tyr Asp Pro Ser Lys Met
            180                 185                 190

Lys Ala Val Ile Tyr Ser Lys His Phe Trp Ser Gly Gln Asp Gln Arg
        195                 200                 205

Gly Ser Ser Asp Lys Arg Lys Tyr Gly Asp Pro Glu Ala Phe Arg Pro
    210                 215                 220

Asp Gln Gly Thr Gly Leu Val Asp Met Ser Lys Asp Arg Ser Ile Pro
225                 230                 235                 240

Arg Ser Pro Ala Lys Pro Gly Glu Gly Trp Val Asn Phe Asp Tyr Gly
                245                 250                 255

Trp Phe Gly Ala Gln Thr Glu Ala Asp Ala Asp Lys Thr Thr Trp Thr
            260                 265                 270

His Gly Asp His Tyr His Ala Pro Asn Ser Asp Leu Gly Pro Met His
        275                 280                 285

Val His Glu Ser Lys Phe Arg Lys Trp Ser Ala Gly Tyr Ala Asp Phe
    290                 295                 300

Asp Arg Gly Ala Tyr Val Ile Thr Phe Ile Pro Lys Ser Trp Asn Thr
305                 310                 315                 320

Ala Pro Ala Lys Val Glu Gln Gly Trp Pro
                325                 330

<210> SEQ ID NO 5
<211> LENGTH: 996
<212> TYPE: DNA
<213> ORGANISM: Streptomyces fradiae
<220> FEATURE:
<221> NAME/KEY: CDS
<222> LOCATION: (1)..(996)

<400> SEQUENCE: 5 gcc ctg gtc gac gac agg gaa acc cct ccc gcc gag ccg ctc gac agg       48
Ala Leu Val Asp Asp Arg Glu Thr Pro Pro Ala Glu Pro Leu Asp Arg
1               5                   10                  15 atg ccc gac gcg tac cgg gcc tac gga ggc aga gcc act acg gtc gtc       96
Met Pro Asp Ala Tyr Arg Ala Tyr Gly Gly Arg Ala Thr Thr Val Val
            20                  25                  30 aac aac tac ata cgc aag tgg cag cag gtc tac agt cag cgc gac ggc      144
Asn Asn Tyr Ile Arg Lys Trp Gln Gln Val Tyr Ser Gln Arg Asp Gly
        35                  40                  45 aag aag cag caa atg acc gaa gag cag cga gag aac ctg tcc tac ggt      192
Lys Lys Gln Gln Met Thr Glu Glu Gln Arg Glu Asn Leu Ser Tyr Gly
    50                  55                  60 tgc gtc ggc gtc acc tgg atc aat tca ggc ttc tac ccg acg aac aaa      240
```

```
Cys Val Gly Val Thr Trp Ile Asn Ser Gly Phe Tyr Pro Thr Asn Lys
 65                  70                  75                  80 ttg gcg ttc gcg ttc ttc gac gag aac aag tac aag aac gat ctg aag    288
Leu Ala Phe Ala Phe Phe Asp Glu Asn Lys Tyr Lys Asn Asp Leu Lys
                 85                  90                  95 aat acc agc ccc cga ccc aat gaa acg cgg gcg gag ttc gag ggc cgc    336
Asn Thr Ser Pro Arg Pro Asn Glu Thr Arg Ala Glu Phe Glu Gly Arg
            100                 105                 110 atc gcc aag gcc agc ttc gac gag ggg aag ggc ttc aag cgg gcg cgt    384
Ile Ala Lys Ala Ser Phe Asp Glu Gly Lys Gly Phe Lys Arg Ala Arg
        115                 120                 125 gat gtg gcc tcc atc atg aac aag gcc ctg gag aac gcc ccc gac gag    432
Asp Val Ala Ser Ile Met Asn Lys Ala Leu Glu Asn Ala Pro Asp Glu
    130                 135                 140 gga acg tac ctc aag aac ctc aag acg gac ctc acg aac aaa aat gat    480
Gly Thr Tyr Leu Lys Asn Leu Lys Thr Asp Leu Thr Asn Lys Asn Asp
145                 150                 155                 160 gcc ctg ctc cac gag gac agc cgc tcg aac ttc tac tcg gca ctg agg    528
Ala Leu Leu His Glu Asp Ser Arg Ser Asn Phe Tyr Ser Ala Leu Arg
                165                 170                 175 aat aca ccg tcc ttc agg gaa aga gac gga ggc aac tac gac ccg tcc    576
Asn Thr Pro Ser Phe Arg Glu Arg Asp Gly Gly Asn Tyr Asp Pro Ser
            180                 185                 190 aag atg aag gcg gtg atc tac tcc aag cac ttc tgg agc ggg cag gac    624
Lys Met Lys Ala Val Ile Tyr Ser Lys His Phe Trp Ser Gly Gln Asp
        195                 200                 205 cag cgg ggc tcc gcc gac aag aga aag tac ggc gac gcg gaa gct ttc    672
Gln Arg Gly Ser Ala Asp Lys Arg Lys Tyr Gly Asp Ala Glu Ala Phe
    210                 215                 220 cgc ccc gac cag ggc acc ggc ctg gtc gac atg tcg aag gac aga aac    720
Arg Pro Asp Gln Gly Thr Gly Leu Val Asp Met Ser Lys Asp Arg Asn
225                 230                 235                 240 att ccg cgc agt ccg gcc cgt cct ggc gaa ggt tgg gtc aat ttc gac    768
Ile Pro Arg Ser Pro Ala Arg Pro Gly Glu Gly Trp Val Asn Phe Asp
                245                 250                 255 tac ggg tgg ttc ggg gct caa acg gca gcg gac gcc gac gaa aca aca    816
Tyr Gly Trp Phe Gly Ala Gln Thr Ala Ala Asp Ala Asp Glu Thr Thr
            260                 265                 270 tgg acc cac ggc gac cac tat cac gca ccc aat agc ggc ctg ggc ccc    864
Trp Thr His Gly Asp His Tyr His Ala Pro Asn Ser Gly Leu Gly Pro
        275                 280                 285 atg cat gtc cac gag agc aag ttc cgg aag tgg tcc gcc ggg tac gcg    912
Met His Val His Glu Ser Lys Phe Arg Lys Trp Ser Ala Gly Tyr Ala
    290                 295                 300 gac ttc gac cgc gga acc tac gtg atc acg ttt ata ccc aag agc tgg    960
Asp Phe Asp Arg Gly Thr Tyr Val Ile Thr Phe Ile Pro Lys Ser Trp
305                 310                 315                 320 aac acc gcc ccc gac aag gtg gag caa ggc tgg ccg                    996
Asn Thr Ala Pro Asp Lys Val Glu Gln Gly Trp Pro
                325                 330

<210> SEQ ID NO 6
<211> LENGTH: 332
<212> TYPE: PRT
<213> ORGANISM: Streptomyces fradiae

<400> SEQUENCE: 6

Ala Leu Val Asp Asp Arg Glu Thr Pro Pro Ala Glu Pro Leu Asp Arg
1               5                   10                  15

Met Pro Asp Ala Tyr Arg Ala Tyr Gly Gly Arg Ala Thr Thr Val Val
            20                  25                  30
```

Asn Asn Tyr Ile Arg Lys Trp Gln Gln Val Tyr Ser Gln Arg Asp Gly
            35                  40                  45

Lys Lys Gln Gln Met Thr Glu Glu Gln Arg Glu Asn Leu Ser Tyr Gly
 50                  55                  60

Cys Val Gly Val Thr Trp Ile Asn Ser Gly Phe Pro Thr Asn Lys
 65                  70                  75                  80

Leu Ala Phe Ala Phe Phe Asp Glu Asn Lys Tyr Lys Asn Asp Leu Lys
                 85                  90                  95

Asn Thr Ser Pro Arg Pro Asn Glu Thr Arg Ala Glu Phe Glu Gly Arg
            100                 105                 110

Ile Ala Lys Ala Ser Phe Asp Glu Gly Lys Gly Phe Lys Arg Ala Arg
            115                 120                 125

Asp Val Ala Ser Ile Met Asn Lys Ala Leu Glu Asn Ala Pro Asp Glu
            130                 135                 140

Gly Thr Tyr Leu Lys Asn Leu Lys Thr Asp Leu Thr Asn Lys Asn Asp
145                 150                 155                 160

Ala Leu Leu His Glu Asp Ser Arg Ser Asn Phe Tyr Ser Ala Leu Arg
                165                 170                 175

Asn Thr Pro Ser Phe Arg Glu Arg Asp Gly Gly Asn Tyr Asp Pro Ser
            180                 185                 190

Lys Met Lys Ala Val Ile Tyr Ser Lys His Phe Trp Ser Gly Gln Asp
            195                 200                 205

Gln Arg Gly Ser Ala Asp Lys Arg Lys Tyr Gly Asp Ala Glu Ala Phe
            210                 215                 220

Arg Pro Asp Gln Gly Thr Gly Leu Val Asp Met Ser Lys Asp Arg Asn
225                 230                 235                 240

Ile Pro Arg Ser Pro Ala Arg Pro Gly Glu Gly Trp Val Asn Phe Asp
                245                 250                 255

Tyr Gly Trp Phe Gly Ala Gln Thr Ala Ala Asp Ala Asp Glu Thr Thr
            260                 265                 270

Trp Thr His Gly Asp His Tyr His Ala Pro Asn Ser Gly Leu Gly Pro
            275                 280                 285

Met His Val His Glu Ser Lys Phe Arg Lys Trp Ser Ala Gly Tyr Ala
            290                 295                 300

Asp Phe Asp Arg Gly Thr Tyr Val Ile Thr Phe Ile Pro Lys Ser Trp
305                 310                 315                 320

Asn Thr Ala Pro Asp Lys Val Glu Gln Gly Trp Pro
                325                 330

<210> SEQ ID NO 7
<211> LENGTH: 993
<212> TYPE: DNA
<213> ORGANISM: Streptomyces ladakanum
<220> FEATURE:
<221> NAME/KEY: CDS
<222> LOCATION: (1)..(993)

<400> SEQUENCE: 7 gac tcc gac gag cgg gtg act cct ccc gcc gag ccg ctc gac cgg atg    48
Asp Ser Asp Glu Arg Val Thr Pro Pro Ala Glu Pro Leu Asp Arg Met
1               5                   10                  15 ccc gac ccg tac cgg ccc tcg tac ggc agg gcc gag acg atc gtc aac    96
Pro Asp Pro Tyr Arg Pro Ser Tyr Gly Arg Ala Glu Thr Ile Val Asn
            20                  25                  30 aac tac ata cgc aag tgg cag cag gtc tac agc cac cgc gac ggc agg   144
Asn Tyr Ile Arg Lys Trp Gln Gln Val Tyr Ser His Arg Asp Gly Arg
        35                  40                  45

```
aaa cag cag atg acc gag gaa cag cgg gag tgg ctg tcc tac ggt tgc      192
Lys Gln Gln Met Thr Glu Glu Gln Arg Glu Trp Leu Ser Tyr Gly Cys
 50                  55                  60 gtc ggt gtc acc tgg gtc aac tcg ggc cag tat ccg acg aac agg ctg      240
Val Gly Val Thr Trp Val Asn Ser Gly Gln Tyr Pro Thr Asn Arg Leu
 65                  70                  75                  80 gct ttc gcg ttc ttc gac gag gac aag tac aag aac gag ctg aag aac      288
Ala Phe Ala Phe Phe Asp Glu Asp Lys Tyr Lys Asn Glu Leu Lys Asn
                 85                  90                  95 ggc agg ccc cgg tcc ggc gaa acg cgg gcg gag ttc gag ggc cgc gtc      336
Gly Arg Pro Arg Ser Gly Glu Thr Arg Ala Glu Phe Glu Gly Arg Val
            100                 105                 110 gcc aag gac agc ttc gac gag gcg aag ggg ttc cag cgg gcg cgt gac      384
Ala Lys Asp Ser Phe Asp Glu Ala Lys Gly Phe Gln Arg Ala Arg Asp
        115                 120                 125 gtg gcg tcc gtc atg aac aag gcc ctg gag aac gcc cac gac gag ggg      432
Val Ala Ser Val Met Asn Lys Ala Leu Glu Asn Ala His Asp Glu Gly
130                 135                 140 gcg tac ctc gac aac ctc aag aag gag ctg gcg aac ggc aac gac gcc      480
Ala Tyr Leu Asp Asn Leu Lys Lys Glu Leu Ala Asn Gly Asn Asp Ala
145                 150                 155                 160 ctg cgg aac gag gat gcc cgc tcg ccc ttc tac tcg gcg ctg cgg aac      528
Leu Arg Asn Glu Asp Ala Arg Ser Pro Phe Tyr Ser Ala Leu Arg Asn
                165                 170                 175 acg ccg tcc ttc aag gac cgc aac ggc ggt aat cac gac ccg tcc aag      576
Thr Pro Ser Phe Lys Asp Arg Asn Gly Gly Asn His Asp Pro Ser Lys
            180                 185                 190 atg aag gcc gtc atc tac tcg aag cac ttc tgg agc ggc cag gac cgg      624
Met Lys Ala Val Ile Tyr Ser Lys His Phe Trp Ser Gly Gln Asp Arg
        195                 200                 205 tcg ggc tcc tcc gac aag agg aag tac ggc gac ccg gag gcc ttc cgc      672
Ser Gly Ser Ser Asp Lys Arg Lys Tyr Gly Asp Pro Glu Ala Phe Arg
210                 215                 220 ccc gac cgc ggc acc ggc ctg gtc gac atg tcg agg gac agg aac att      720
Pro Asp Arg Gly Thr Gly Leu Val Asp Met Ser Arg Asp Arg Asn Ile
225                 230                 235                 240 ccg cgc agc ccc acc agc ccc ggc gag agt ttc gtc aat ttc gac tac      768
Pro Arg Ser Pro Thr Ser Pro Gly Glu Ser Phe Val Asn Phe Asp Tyr
                245                 250                 255 ggc tgg ttc gga gcg cag acg gaa gcg gac gcc gac aag acc gta tgg      816
Gly Trp Phe Gly Ala Gln Thr Glu Ala Asp Ala Asp Lys Thr Val Trp
            260                 265                 270 acc cac ggc aac cac tac cac gcg ccc aat ggc agc ctg ggt gcc atg      864
Thr His Gly Asn His Tyr His Ala Pro Asn Gly Ser Leu Gly Ala Met
        275                 280                 285 cac gtg tac gag agc aag ttc cgc aac tgg tcc gac ggt tac tcg gac      912
His Val Tyr Glu Ser Lys Phe Arg Asn Trp Ser Asp Gly Tyr Ser Asp
290                 295                 300 ttc gac cgc gga gcc tac gtg gtc acg ttc gtc ccc aag agc tgg aac      960
Phe Asp Arg Gly Ala Tyr Val Val Thr Phe Val Pro Lys Ser Trp Asn
305                 310                 315                 320 acc gcc ccc gac aag gtg aca cag ggc tgg ccg                          993
Thr Ala Pro Asp Lys Val Thr Gln Gly Trp Pro
                325                 330
```

<210> SEQ ID NO 8
<211> LENGTH: 331
<212> TYPE: PRT
<213> ORGANISM: Streptomyces ladakanum

<400> SEQUENCE: 8

```
Asp Ser Asp Glu Arg Val Thr Pro Pro Ala Glu Pro Leu Asp Arg Met
1               5                   10                  15

Pro Asp Pro Tyr Arg Pro Ser Tyr Gly Arg Ala Glu Thr Ile Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65              70                  75                  80

Ala Phe Ala Phe Phe Asp Glu Asp Lys Tyr Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Asp Ser Phe Asp Glu Ala Lys Gly Phe Gln Arg Ala Arg Asp
        115                 120                 125

Val Ala Ser Val Met Asn Lys Ala Leu Glu Asn Ala His Asp Glu Gly
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Asp Arg Asn Gly Gly Asn His Asp Pro Ser Lys
            180                 185                 190

Met Lys Ala Val Ile Tyr Ser Lys His Phe Trp Ser Gly Gln Asp Arg
        195                 200                 205

Ser Gly Ser Ser Asp Lys Arg Lys Tyr Gly Asp Pro Glu Ala Phe Arg
    210                 215                 220

Pro Asp Arg Gly Thr Gly Leu Val Asp Met Ser Arg Asp Arg Asn Ile
225                 230                 235                 240

Pro Arg Ser Pro Thr Ser Pro Gly Glu Ser Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Asp Gly Tyr Ser Asp
    290                 295                 300

Phe Asp Arg Gly Ala Tyr Val Val Thr Phe Val Pro Lys Ser Trp Asn
305                 310                 315                 320

Thr Ala Pro Asp Lys Val Thr Gln Gly Trp Pro
                325                 330
```

<210> SEQ ID NO 9
<211> LENGTH: 993
<212> TYPE: DNA
<213> ORGANISM: Streptomyces lydicus
<220> FEATURE:
<221> NAME/KEY: CDS
<222> LOCATION: (1)..(993)

<400> SEQUENCE: 9

```
gca gcc gac gaa agg gtc acc cct ccc gcc gag ccg ctc aac cgg atg      48
Ala Ala Asp Glu Arg Val Thr Pro Pro Ala Glu Pro Leu Asn Arg Met
1               5                   10                  15 cct gac gcg tac cgg gcc tac gga ggt agg gcc act acg gtc gtc aac      96
```

```
            Pro Asp Ala Tyr Arg Ala Tyr Gly Gly Arg Ala Thr Thr Val Val Asn
                         20                  25                  30 aac tac ata cgc aag tgg cag cag gtc tac agt cac cgc gac ggc atc          144
Asn Tyr Ile Arg Lys Trp Gln Gln Val Tyr Ser His Arg Asp Gly Ile
             35                  40                  45 caa cag caa atg acc gaa gag cag cga gaa aag ctg tcc tac ggc tgc          192
Gln Gln Gln Met Thr Glu Glu Gln Arg Glu Lys Leu Ser Tyr Gly Cys
         50                  55                  60 gtc ggc atc acc tgg gtc aat tcg ggc ccc tac ccg acg aat aaa ttg          240
Val Gly Ile Thr Trp Val Asn Ser Gly Pro Tyr Pro Thr Asn Lys Leu
65                  70                  75                  80 gcg ttc gcg ttc ttc gac gag aac aag tac aag agt gac ctg gaa aac          288
Ala Phe Ala Phe Phe Asp Glu Asn Lys Tyr Lys Ser Asp Leu Glu Asn
                 85                  90                  95 agc agg cca cgc ccc aat gag acg caa gcc gag ttt gag ggg cgc atc          336
Ser Arg Pro Arg Pro Asn Glu Thr Gln Ala Glu Phe Glu Gly Arg Ile
             100                 105                 110 gtc aag gac agt ttc gac gag ggg aag ggt ttc aag cgg gcg cgt gat          384
Val Lys Asp Ser Phe Asp Glu Gly Lys Gly Phe Lys Arg Ala Arg Asp
         115                 120                 125 gtg gcg tcc gtc atg aac aag gcc ctg gat agt gcg cac gac gag ggg          432
Val Ala Ser Val Met Asn Lys Ala Leu Asp Ser Ala His Asp Glu Gly
     130                 135                 140 act tac atc gac aac ctc aag acg gag ctc gcg aac aaa aat gac gct          480
Thr Tyr Ile Asp Asn Leu Lys Thr Glu Leu Ala Asn Lys Asn Asp Ala
145                 150                 155                 160 ctg cgc tac gag gac ggt cgc tcg aac ttt tac tcg gcg ctg agg aat          528
Leu Arg Tyr Glu Asp Gly Arg Ser Asn Phe Tyr Ser Ala Leu Arg Asn
                 165                 170                 175 acg ccg tcc ttc aag gaa agg gat gga ggt aac tac gac cca tcc aag          576
Thr Pro Ser Phe Lys Glu Arg Asp Gly Gly Asn Tyr Asp Pro Ser Lys
             180                 185                 190 atg aag gcg gtg gtc tac tcg aaa cac ttc tgg agc ggg cag gac cag          624
Met Lys Ala Val Val Tyr Ser Lys His Phe Trp Ser Gly Gln Asp Gln
         195                 200                 205 cgg ggc tcc tct gac aag agg aag tac ggc gac ccg gat gcc ttc cgc          672
Arg Gly Ser Ser Asp Lys Arg Lys Tyr Gly Asp Pro Asp Ala Phe Arg
     210                 215                 220 ccc gac cag ggc aca ggc ctg gta gac atg tcg aag gac agg aat att          720
Pro Asp Gln Gly Thr Gly Leu Val Asp Met Ser Lys Asp Arg Asn Ile
225                 230                 235                 240 ccg cgc agt ccc gcc caa cct ggc gaa agt tgg gtc aat ttc gac tac          768
Pro Arg Ser Pro Ala Gln Pro Gly Glu Ser Trp Val Asn Phe Asp Tyr
                 245                 250                 255 ggc tgg ttt ggg gct cag acg gaa tcg gac gcc gac aaa acc ata tgg          816
Gly Trp Phe Gly Ala Gln Thr Glu Ser Asp Ala Asp Lys Thr Ile Trp
             260                 265                 270 acc cac gcc aac cac tat cac gcg ccc aac ggc ggc ctg ggc ccc atg          864
Thr His Ala Asn His Tyr His Ala Pro Asn Gly Gly Leu Gly Pro Met
         275                 280                 285 aac gta tat gag agc aag ttc cgg aac tgg tct gcc ggg tac gcg gat          912
Asn Val Tyr Glu Ser Lys Phe Arg Asn Trp Ser Ala Gly Tyr Ala Asp
     290                 295                 300 ttc gac cgc gga acc tac gtc atc acg ttc ata ccc aag agc tgg aac          960
Phe Asp Arg Gly Thr Tyr Val Ile Thr Phe Ile Pro Lys Ser Trp Asn
305                 310                 315                 320 acc gcc ccc gcc gag gta aag cag ggc tgg tcg                              993
Thr Ala Pro Ala Glu Val Lys Gln Gly Trp Ser
                 325                 330
```

<210> SEQ ID NO 10
<211> LENGTH: 331
<212> TYPE: PRT
<213> ORGANISM: Streptomyces lydicus

<400> SEQUENCE: 10

```
Ala Ala Asp Glu Arg Val Thr Pro Pro Ala Glu Pro Leu Asn Arg Met
1               5                   10                  15

Pro Asp Ala Tyr Arg Ala Tyr Gly Gly Arg Ala Thr Thr Val Val Asn
            20                  25                  30

Asn Tyr Ile Arg Lys Trp Gln Gln Val Tyr Ser His Arg Asp Gly Ile
        35                  40                  45

Gln Gln Gln Met Thr Glu Glu Gln Arg Glu Lys Leu Ser Tyr Gly Cys
    50                  55                  60

Val Gly Ile Thr Trp Val Asn Ser Gly Pro Tyr Pro Thr Asn Lys Leu
65                  70                  75                  80

Ala Phe Ala Phe Phe Asp Glu Asn Lys Tyr Lys Ser Asp Leu Glu Asn
                85                  90                  95

Ser Arg Pro Arg Pro Asn Glu Thr Gln Ala Glu Phe Glu Gly Arg Ile
            100                 105                 110

Val Lys Asp Ser Phe Asp Glu Gly Lys Gly Phe Lys Arg Ala Arg Asp
        115                 120                 125

Val Ala Ser Val Met Asn Lys Ala Leu Asp Ser Ala His Asp Glu Gly
    130                 135                 140

Thr Tyr Ile Asp Asn Leu Lys Thr Glu Leu Ala Asn Lys Asn Asp Ala
145                 150                 155                 160

Leu Arg Tyr Glu Asp Gly Arg Ser Asn Phe Tyr Ser Ala Leu Arg Asn
                165                 170                 175

Thr Pro Ser Phe Lys Glu Arg Asp Gly Gly Asn Tyr Asp Pro Ser Lys
            180                 185                 190

Met Lys Ala Val Val Tyr Ser Lys His Phe Trp Ser Gly Gln Asp Gln
        195                 200                 205

Arg Gly Ser Ser Asp Lys Arg Lys Tyr Gly Asp Pro Asp Ala Phe Arg
    210                 215                 220

Pro Asp Gln Gly Thr Gly Leu Val Asp Met Ser Lys Asp Arg Asn Ile
225                 230                 235                 240

Pro Arg Ser Pro Ala Gln Pro Gly Glu Ser Trp Val Asn Phe Asp Tyr
                245                 250                 255

Gly Trp Phe Gly Ala Gln Thr Glu Ser Asp Ala Asp Lys Thr Ile Trp
            260                 265                 270

Thr His Ala Asn His Tyr His Ala Pro Asn Gly Gly Leu Gly Pro Met
        275                 280                 285

Asn Val Tyr Glu Ser Lys Phe Arg Asn Trp Ser Ala Gly Tyr Ala Asp
    290                 295                 300

Phe Asp Arg Gly Thr Tyr Val Ile Thr Phe Ile Pro Lys Ser Trp Asn
305                 310                 315                 320

Thr Ala Pro Ala Glu Val Lys Gln Gly Trp Ser
                325                 330
```

<210> SEQ ID NO 11
<211> LENGTH: 996
<212> TYPE: DNA
<213> ORGANISM: Streptomyces platensis
<220> FEATURE:
<221> NAME/KEY: CDS
<222> LOCATION: (1)..(996)

<400> SEQUENCE: 11

```
gac gcc gtc gat gac agg gtg acc cct ccc gcc gag ccg ctc aac cgg      48
Asp Ala Val Asp Asp Arg Val Thr Pro Pro Ala Glu Pro Leu Asn Arg
1               5                   10                  15 atg cct gac gcg tac cgg gcc tac gga ggc agg gcc act acg gtc gtc      96
Met Pro Asp Ala Tyr Arg Ala Tyr Gly Gly Arg Ala Thr Thr Val Val
                20                  25                  30 aac aac tac ata cgc aag tgg cag cag gtc tac agt caa cgc ggc ggc     144
Asn Asn Tyr Ile Arg Lys Trp Gln Gln Val Tyr Ser Gln Arg Gly Gly
            35                  40                  45 aac cca cag caa atg acc gaa gag cag cga gaa caa ctg tcc tac ggc     192
Asn Pro Gln Gln Met Thr Glu Glu Gln Arg Glu Gln Leu Ser Tyr Gly
        50                  55                  60 tgc gtc ggc gtc acc tgg gtc aat aca ggc ccc tac ccg acg aac aaa     240
Cys Val Gly Val Thr Trp Val Asn Thr Gly Pro Tyr Pro Thr Asn Lys
65                  70                  75                  80 ctc gcg ttc gcg ttc ttc gac gag aac aag tac aag aac gac ctg gaa     288
Leu Ala Phe Ala Phe Phe Asp Glu Asn Lys Tyr Lys Asn Asp Leu Glu
                85                  90                  95 aac agc aga ccg cga ccc aac gag acg cag gcg gag ttc gag ggg cgc     336
Asn Ser Arg Pro Arg Pro Asn Glu Thr Gln Ala Glu Phe Glu Gly Arg
            100                 105                 110 atc gcc aag gac agt ttc gat gag gga aag ggt ttc aag cgg gcg cgt     384
Ile Ala Lys Asp Ser Phe Asp Glu Gly Lys Gly Phe Lys Arg Ala Arg
        115                 120                 125 gag gtg gca tcc gtc atg aac aag gcc ctg gat aac gcg cac gac gag     432
Glu Val Ala Ser Val Met Asn Lys Ala Leu Asp Asn Ala His Asp Glu
    130                 135                 140 gag act tac atc ggc cac ctc aag aca gag ctc gcg aac aaa aac gac     480
Glu Thr Tyr Ile Gly His Leu Lys Thr Glu Leu Ala Asn Lys Asn Asp
145                 150                 155                 160 gct ctg ctc tac gag gac agc cgc tcg agc ttt tac tcg gcg ctg agg     528
Ala Leu Leu Tyr Glu Asp Ser Arg Ser Ser Phe Tyr Ser Ala Leu Arg
                165                 170                 175 aat acg ccg tcc ttc aag gaa agg gat gga ggc aac tac gac ccg tcc     576
Asn Thr Pro Ser Phe Lys Glu Arg Asp Gly Gly Asn Tyr Asp Pro Ser
            180                 185                 190 aag atg aag gcg gtg gtc tac tcg aag cac ttc tgg agc ggg cag gac     624
Lys Met Lys Ala Val Val Tyr Ser Lys His Phe Trp Ser Gly Gln Asp
        195                 200                 205 cag cgg ggc tcc tcc gag aag agg aag tac ggt gac ccg gac gcc ttc     672
Gln Arg Gly Ser Ser Glu Lys Arg Lys Tyr Gly Asp Pro Asp Ala Phe
    210                 215                 220 cgc ccc ggc cag ggc aca ggt ctg gta gac atg tcg agg gac agg aac     720
Arg Pro Gly Gln Gly Thr Gly Leu Val Asp Met Ser Arg Asp Arg Asn
225                 230                 235                 240 att ccg cgt agt ccc gca aaa cct ggc gaa agt tgg gtc aat ttc gac     768
Ile Pro Arg Ser Pro Ala Lys Pro Gly Glu Ser Trp Val Asn Phe Asp
                245                 250                 255 tac ggc tgg ttc ggg gct cag gca gaa gcg gat gcc gac aaa acc gta     816
Tyr Gly Trp Phe Gly Ala Gln Ala Glu Ala Asp Ala Asp Lys Thr Val
            260                 265                 270 tgg acc cac gcc aac cac tat cat gcg ccc aat ggc ggc atg ggc ccc     864
Trp Thr His Ala Asn His Tyr His Ala Pro Asn Gly Gly Met Gly Pro
        275                 280                 285 atg aac gta tac gag agc aag ttc cgg aac tgg tct gcg ggg tac gcg     912
Met Asn Val Tyr Glu Ser Lys Phe Arg Asn Trp Ser Ala Gly Tyr Ala
    290                 295                 300 gac ttc gac cgc gga gcc tac gtc atc acg ttc ata ccc aag agc tgg     960
Asp Phe Asp Arg Gly Ala Tyr Val Ile Thr Phe Ile Pro Lys Ser Trp
305                 310                 315                 320
```

```
aac acc gcc ccc gcc gag gtg aag cag ggc tgg ccg                              996
Asn Thr Ala Pro Ala Glu Val Lys Gln Gly Trp Pro
                325                 330
```

<210> SEQ ID NO 12
<211> LENGTH: 332
<212> TYPE: PRT
<213> ORGANISM: Streptomyces platensis

<400> SEQUENCE: 12

```
Asp Ala Val Asp Arg Val Thr Pro Pro Ala Glu Pro Leu Asn Arg
1               5                   10                  15

Met Pro Asp Ala Tyr Arg Ala Tyr Gly Gly Arg Ala Thr Thr Val Val
                20                  25                  30

Asn Asn Tyr Ile Arg Lys Trp Gln Gln Val Tyr Ser Gln Arg Gly Gly
            35                  40                  45

Asn Pro Gln Gln Met Thr Glu Glu Gln Arg Glu Gln Leu Ser Tyr Gly
        50                  55                  60

Cys Val Gly Val Thr Trp Val Asn Thr Gly Pro Tyr Pro Thr Asn Lys
65              70                  75                  80

Leu Ala Phe Ala Phe Asp Glu Asn Lys Tyr Lys Asn Asp Leu Glu
                85                  90                  95

Asn Ser Arg Pro Arg Pro Asn Glu Thr Gln Ala Glu Phe Glu Gly Arg
            100                 105                 110

Ile Ala Lys Asp Ser Phe Asp Glu Gly Lys Gly Phe Lys Arg Ala Arg
        115                 120                 125

Glu Val Ala Ser Val Met Asn Lys Ala Leu Asp Asn Ala His Asp Glu
130                 135                 140

Glu Thr Tyr Ile Gly His Leu Lys Thr Glu Leu Ala Asn Lys Asn Asp
145                 150                 155                 160

Ala Leu Leu Tyr Glu Asp Ser Arg Ser Phe Tyr Ser Ala Leu Arg
                165                 170                 175

Asn Thr Pro Ser Phe Lys Glu Arg Asp Gly Gly Asn Tyr Asp Pro Ser
            180                 185                 190

Lys Met Lys Ala Val Val Tyr Ser Lys His Phe Trp Ser Gly Gln Asp
        195                 200                 205

Gln Arg Gly Ser Ser Glu Lys Arg Lys Tyr Gly Asp Pro Asp Ala Phe
    210                 215                 220

Arg Pro Gly Gln Gly Thr Gly Leu Val Asp Met Ser Arg Asp Arg Asn
225                 230                 235                 240

Ile Pro Arg Ser Pro Ala Lys Pro Gly Glu Ser Trp Val Asn Phe Asp
                245                 250                 255

Tyr Gly Trp Phe Gly Ala Gln Ala Glu Ala Asp Ala Asp Lys Thr Val
            260                 265                 270

Trp Thr His Ala Asn His Tyr His Ala Pro Asn Gly Gly Met Gly Pro
        275                 280                 285

Met Asn Val Tyr Glu Ser Lys Phe Arg Asn Trp Ser Ala Gly Tyr Ala
    290                 295                 300

Asp Phe Asp Arg Gly Ala Tyr Val Ile Thr Phe Ile Pro Lys Ser Trp
305                 310                 315                 320

Asn Thr Ala Pro Ala Glu Val Lys Gln Gly Trp Pro
                325                 330
```

<210> SEQ ID NO 13
<211> LENGTH: 18
<212> TYPE: DNA

```
<213> ORGANISM: Artificial
<220> FEATURE:
<223> OTHER INFORMATION: forward primer

<400> SEQUENCE: 13
tccatagcaa tccaaagg                                                         18

<210> SEQ ID NO 14
<211> LENGTH: 30
<212> TYPE: DNA
<213> ORGANISM: Artificial
<220> FEATURE:
<223> OTHER INFORMATION: reverse primer

<400> SEQUENCE: 14
gggcgaccga gaagtttttt acaaaaggca                                            30
```